(12) United States Patent
Pintor et al.

(10) Patent No.: US 9,370,418 B2
(45) Date of Patent: Jun. 21, 2016

(54) RAPIDLY DEPLOYABLE SURGICAL HEART VALVES

(71) Applicant: Edwards Lifesciences Corporation, Irvine, CA (US)

(72) Inventors: Rafael Pintor, Mission Viejo, CA (US); Michael J. Scott, San Diego, CA (US); Qinggang Zeng, Irvine, CA (US); Grace Myong Kim, Seal Beach, CA (US); Visith Chung, Chino Hills, CA (US); Louis A. Campbell, Santa Ana, CA (US); David S. Lin, Irvine, CA (US); Peng Norasing, Corona, CA (US); Edwin T. Ta, Irvine, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 43 days.

(21) Appl. No.: 13/797,591

(22) Filed: Mar. 12, 2013

(65) Prior Publication Data
US 2013/0190862 A1 Jul. 25, 2013

Related U.S. Application Data

(63) Continuation-in-part of application No. 13/167,639, filed on Jun. 23, 2011, now Pat. No. 8,641,757.

(60) Provisional application No. 61/381,931, filed on Sep. 10, 2010.

(51) Int. Cl.
A61F 2/24 (2006.01)

(52) U.S. Cl.
CPC ............. *A61F 2/2403* (2013.01); *A61F 2/2412* (2013.01); *A61F 2/2418* (2013.01);
(Continued)

(58) Field of Classification Search
CPC ..... A61F 2/2403; A61F 2/2412; A61F 2/2418; A61F 2/2433
USPC ....................... 623/1.24–1.26, 2.11–2.18, 900
See application file for complete search history.

(56) References Cited

U.S. PATENT DOCUMENTS

| 3,143,742 A | 8/1964 | Cromie |
|---|---|---|
| 3,320,972 A | 5/1967 | High et al. |

(Continued)

FOREIGN PATENT DOCUMENTS

| CN | 2356656 Y | 1/2000 |
|---|---|---|
| EP | 0084395 A1 | 7/1983 |

(Continued)

OTHER PUBLICATIONS

Krakow, "3F Therapeutics, Inc. Announces the First Clinical Implantation of the 3F Enable Aortic Heart Valve, a Patented, Sutureless Implantation, Replacement Heart Valve Intended to Save Valuable Surgery Time and Reduce Time Related Complications . . . " Healthcare Sales & Marketing Network News Feed, Jan. 18, 2005, pp. 1-2.

(Continued)

*Primary Examiner* — Eric Rosen
*Assistant Examiner* — Mikail Mannan
(74) *Attorney, Agent, or Firm* — AnneMarie Kaiser; Guy Cumberbatch; Pui Tong Ho

(57) ABSTRACT

A quick-connect heart valve prosthesis that can be quickly and easily implanted during a surgical procedure is provided. The heart valve includes a substantially non-expandable, non-compressible prosthetic valve and a plastically-expandable stent frame, thereby enabling attachment to the annulus without sutures. The prosthetic valve may be a commercially available valve with a sewing ring and the stent frame attached thereto. The stent frame may expand from a conical deployment shape to a conical expanded shape, and may have a cloth covering its entirety as well as a plush sealing flange around its periphery to prevent paravalvular leaking.

22 Claims, 22 Drawing Sheets

(52) U.S. Cl.
CPC ......... *A61F2/2433* (2013.01); *A61F 2220/005* (2013.01); *A61F 2220/0008* (2013.01); *A61F 2220/0016* (2013.01); *A61F 2220/0075* (2013.01); *A61F 2220/0083* (2013.01)

(56) References Cited

U.S. PATENT DOCUMENTS

| | | | |
|---|---|---|---|
| 3,371,352 A | 3/1968 | Siposs et al. | |
| 3,409,013 A | 11/1968 | Berry | |
| 3,546,710 A | 12/1970 | Shumakov et al. | |
| 3,574,865 A | 4/1971 | Hamaker | |
| 3,628,535 A | 12/1971 | Ostrowsky et al. | |
| 3,657,744 A | 4/1972 | Ersek | |
| 3,686,740 A | 8/1972 | Shiley | |
| 3,755,823 A | 9/1973 | Hancock | |
| 3,839,741 A | 10/1974 | Haller | |
| 3,997,923 A | 12/1976 | Possis | |
| 4,035,849 A | 7/1977 | Angell et al. | |
| 4,078,468 A | 3/1978 | Civitello | |
| 4,079,468 A | 3/1978 | Liotta et al. | |
| 4,084,268 A | 4/1978 | Ionescu et al. | |
| 4,106,129 A | 8/1978 | Carpentier et al. | |
| 4,172,295 A | 10/1979 | Batten | |
| 4,217,665 A | 8/1980 | Bex et al. | |
| 4,218,782 A | 8/1980 | Rygg | |
| 4,259,753 A | 4/1981 | Liotta et al. | |
| RE30,912 E | 4/1982 | Hancock | |
| 4,343,048 A | 8/1982 | Ross et al. | |
| 4,364,126 A | 12/1982 | Rosen et al. | |
| 4,388,735 A | 6/1983 | Ionescu et al. | |
| 4,441,216 A | 4/1984 | Ionescu et al. | |
| 4,451,936 A | 6/1984 | Carpentier et al. | |
| 4,470,157 A | 9/1984 | Love | |
| 4,501,030 A | 2/1985 | Lane | |
| 4,506,394 A | 3/1985 | Bedard | |
| 4,535,483 A | 8/1985 | Klawitter et al. | |
| 4,605,407 A | 8/1986 | Black et al. | |
| 4,626,255 A | 12/1986 | Reichart et al. | |
| 4,629,459 A | 12/1986 | Ionescu et al. | |
| 4,680,031 A | 7/1987 | Alonso | |
| 4,702,250 A | 10/1987 | Ovil et al. | |
| 4,705,516 A | 11/1987 | Barone et al. | |
| 4,725,274 A | 2/1988 | Lane et al. | |
| 4,731,074 A | 3/1988 | Rousseau et al. | |
| 4,759,758 A * | 7/1988 | Gabbay | 623/2.13 |
| 4,778,461 A | 10/1988 | Pietsch et al. | |
| 4,790,843 A | 12/1988 | Carpentier et al. | |
| 4,851,000 A | 7/1989 | Gupta | |
| 4,865,600 A | 9/1989 | Carpentier et al. | |
| 4,888,009 A | 12/1989 | Lederman et al. | |
| 4,914,097 A | 4/1990 | Oda et al. | |
| 4,960,424 A | 10/1990 | Grooters | |
| 4,993,428 A | 2/1991 | Arms | |
| 5,010,892 A | 4/1991 | Colvin et al. | |
| 5,032,128 A | 7/1991 | Alonso | |
| 5,037,434 A | 8/1991 | Lane | |
| 5,147,391 A | 9/1992 | Lane | |
| 5,163,955 A | 11/1992 | Love et al. | |
| 5,258,023 A | 11/1993 | Reger | |
| 5,290,300 A | 3/1994 | Cosgrove et al. | |
| 5,316,016 A | 5/1994 | Adams et al. | |
| 5,326,370 A | 7/1994 | Love et al. | |
| 5,326,371 A | 7/1994 | Love et al. | |
| 5,332,402 A | 7/1994 | Teitelbaum | |
| 5,370,685 A | 12/1994 | Stevens | |
| 5,376,112 A | 12/1994 | Duran | |
| 5,396,887 A | 3/1995 | Imran | |
| 5,397,351 A | 3/1995 | Pavcnik et al. | |
| 5,411,552 A | 5/1995 | Andersen et al. | |
| 5,413,676 A | 5/1995 | Nguyen et al. | |
| 5,423,887 A | 6/1995 | Love et al. | |
| 5,425,741 A | 6/1995 | Lemp et al. | |
| 5,431,676 A | 7/1995 | Dubrul et al. | |
| 5,449,384 A | 9/1995 | Johnson | |
| 5,449,385 A | 9/1995 | Religa et al. | |
| 5,469,868 A | 11/1995 | Reger | |
| 5,476,510 A | 12/1995 | Eberhardt et al. | |
| 5,488,789 A | 2/1996 | Religa et al. | |
| 5,489,297 A | 2/1996 | Duran | |
| 5,489,298 A | 2/1996 | Love et al. | |
| 5,500,016 A | 3/1996 | Fisher | |
| 5,522,884 A | 6/1996 | Wright | |
| 5,531,785 A | 7/1996 | Love et al. | |
| 5,533,515 A | 7/1996 | Coller et al. | |
| 5,549,665 A | 8/1996 | Vesely et al. | |
| 5,562,729 A | 10/1996 | Purdy et al. | |
| 5,571,215 A | 11/1996 | Sterman et al. | |
| 5,573,007 A | 11/1996 | Bobo, Sr. | |
| 5,578,076 A | 11/1996 | Krueger et al. | |
| 5,584,803 A | 12/1996 | Stevens et al. | |
| 5,618,307 A | 4/1997 | Donlon et al. | |
| 5,626,607 A | 5/1997 | Malecki et al. | |
| 5,628,789 A | 5/1997 | Vanney et al. | |
| 5,693,090 A | 12/1997 | Unsworth et al. | |
| 5,695,503 A | 12/1997 | Krueger et al. | |
| 5,713,952 A | 2/1998 | Vanney et al. | |
| 5,716,370 A | 2/1998 | Williamson, IV et al. | |
| 5,728,064 A | 3/1998 | Burns et al. | |
| 5,728,151 A | 3/1998 | Garrison et al. | |
| 5,735,894 A | 4/1998 | Krueger et al. | |
| 5,752,522 A | 5/1998 | Murphy | |
| 5,755,782 A | 5/1998 | Love et al. | |
| 5,766,240 A | 6/1998 | Johnson | |
| 5,776,187 A | 7/1998 | Krueger et al. | |
| 5,776,188 A | 7/1998 | Shepherd et al. | |
| 5,800,527 A | 9/1998 | Jansen et al. | |
| 5,814,097 A | 9/1998 | Sterman et al. | |
| 5,814,098 A | 9/1998 | Hinnenkamp et al. | |
| 5,824,064 A | 10/1998 | Taheri | |
| 5,840,081 A | 11/1998 | Andersen et al. | |
| 5,848,969 A | 12/1998 | Panescu et al. | |
| 5,855,563 A | 1/1999 | Kaplan et al. | |
| 5,855,601 A | 1/1999 | Bessler et al. | |
| 5,865,801 A | 2/1999 | Houser | |
| 5,891,160 A | 4/1999 | Williamson, IV et al. | |
| 5,895,420 A | 4/1999 | Mirsch, II et al. | |
| 5,902,308 A | 5/1999 | Murphy | |
| 5,908,450 A | 6/1999 | Gross et al. | |
| 5,919,147 A | 7/1999 | Jain | |
| 5,921,934 A | 7/1999 | Teo | |
| 5,921,935 A | 7/1999 | Hickey | |
| 5,924,984 A | 7/1999 | Rao | |
| 5,957,949 A | 9/1999 | Leonhardt et al. | |
| 5,972,004 A | 10/1999 | Williamson, IV et al. | |
| 5,984,959 A | 11/1999 | Robertson et al. | |
| 5,984,973 A | 11/1999 | Girard et al. | |
| 6,010,531 A | 1/2000 | Donlon et al. | |
| 6,042,607 A | 3/2000 | Williamson, IV et al. | |
| 6,059,827 A | 5/2000 | Fenton, Jr. | |
| 6,066,160 A | 5/2000 | Colvin et al. | |
| 6,074,418 A | 6/2000 | Buchanan et al. | |
| 6,081,737 A | 6/2000 | Shah | |
| 6,083,179 A | 7/2000 | Oredsson | |
| 6,099,475 A | 8/2000 | Seward et al. | |
| 6,106,550 A | 8/2000 | Magovern et al. | |
| 6,110,200 A | 8/2000 | Hinnenkamp | |
| 6,117,091 A | 9/2000 | Young et al. | |
| 6,162,233 A | 12/2000 | Williamson, IV et al. | |
| 6,168,614 B1 | 1/2001 | Andersen et al. | |
| 6,176,877 B1 | 1/2001 | Buchanan et al. | |
| 6,197,054 B1 | 3/2001 | Hamblin, Jr. et al. | |
| 6,217,611 B1 | 4/2001 | Klostermeyer | |
| 6,231,561 B1 | 5/2001 | Frazier et al. | |
| 6,241,765 B1 | 6/2001 | Griffin et al. | |
| 6,245,102 B1 | 6/2001 | Jayaraman | |
| 6,283,127 B1 | 9/2001 | Sterman et al. | |
| 6,287,339 B1 | 9/2001 | Vazquez et al. | |
| 6,290,674 B1 | 9/2001 | Roue et al. | |
| 6,312,447 B1 | 11/2001 | Grimes | |
| 6,312,465 B1 | 11/2001 | Griffin et al. | |
| 6,328,727 B1 | 12/2001 | Frazier et al. | |
| 6,371,983 B1 | 4/2002 | Lane | |
| 6,402,780 B2 | 6/2002 | Williamson, IV et al. | |
| 6,425,916 B1 | 7/2002 | Garrison et al. | |

(56) References Cited

U.S. PATENT DOCUMENTS

| | | |
|---|---|---|
| 6,440,164 B1 | 8/2002 | DiMatteo et al. |
| 6,447,551 B1 * | 9/2002 | Goldmann ................ 623/23.76 |
| 6,454,799 B1 | 9/2002 | Schreck |
| 6,458,153 B1 | 10/2002 | Bailey et al. |
| 6,468,305 B1 | 10/2002 | Otte |
| 6,530,952 B2 | 3/2003 | Vesely |
| 6,558,429 B2 | 5/2003 | Taylor |
| 6,569,196 B1 | 5/2003 | Vesely |
| 6,585,766 B1 | 7/2003 | Huynh et al. |
| 6,652,578 B2 | 11/2003 | Bailey et al. |
| 6,682,559 B2 | 1/2004 | Myers et al. |
| 6,685,739 B2 | 2/2004 | DiMatteo et al. |
| 6,719,789 B2 | 4/2004 | Cox |
| 6,730,118 B2 | 5/2004 | Spenser et al. |
| 6,733,525 B2 | 5/2004 | Pease et al. |
| 6,764,508 B1 | 7/2004 | Roehe et al. |
| 6,767,362 B2 | 7/2004 | Schreck |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,846,325 B2 | 1/2005 | Liddicoat |
| 6,893,459 B1 | 5/2005 | Macoviak |
| 6,893,460 B2 | 5/2005 | Spenser et al. |
| 6,908,481 B2 | 6/2005 | Cribier |
| 6,936,067 B2 | 8/2005 | Buchanan |
| 6,939,365 B1 | 9/2005 | Fogarty et al. |
| 6,974,476 B2 | 12/2005 | McGuckin, Jr. et al. |
| 7,011,681 B2 | 3/2006 | Vesely |
| 7,018,406 B2 | 3/2006 | Seguin et al. |
| 7,025,780 B2 | 4/2006 | Gabbay |
| 7,070,616 B2 | 7/2006 | Majercak et al. |
| 7,081,131 B2 | 7/2006 | Thornton |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,172,625 B2 | 2/2007 | Shu et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| 7,311,730 B2 | 12/2007 | Gabbay |
| RE40,377 E | 6/2008 | Williamson, IV et al. |
| 7,422,603 B2 | 9/2008 | Lane |
| 7,429,269 B2 | 9/2008 | Schwammenthal et al. |
| 7,442,204 B2 | 10/2008 | Schwammenthal et al. |
| 7,445,630 B2 | 11/2008 | Lashinski et al. |
| 7,468,073 B2 | 12/2008 | Johnson et al. |
| 7,470,285 B2 | 12/2008 | Nugent et al. |
| 7,513,909 B2 | 4/2009 | Lane et al. |
| 7,534,261 B2 | 5/2009 | Friedman |
| 7,556,647 B2 | 7/2009 | Drews et al. |
| 7,569,072 B2 | 8/2009 | Berg et al. |
| 7,578,843 B2 | 8/2009 | Shu |
| 7,585,321 B2 | 9/2009 | Cribier |
| 7,597,711 B2 | 10/2009 | Drews et al. |
| 7,611,535 B2 | 11/2009 | Woolfson et al. |
| 7,682,390 B2 | 3/2010 | Seguin |
| 8,308,798 B2 | 11/2012 | Pintor et al. |
| 8,348,998 B2 | 1/2013 | Pintor et al. |
| 8,353,953 B2 | 1/2013 | Giannetti et al. |
| 2001/0021872 A1 | 9/2001 | Bailey et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0137702 A1 | 6/2005 | Haug et al. |
| 2005/0151970 A1 | 7/2005 | DeGeorge et al. |
| 2005/0159811 A1 | 7/2005 | Lane |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240259 A1 | 10/2005 | Sisken et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |

(56) References Cited

U.S. PATENT DOCUMENTS

| | | |
|---|---|---|
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0122692 A1 | 6/2006 | Gilad et al. |
| 2006/0136054 A1 | 6/2006 | Berg et al. |
| 2006/0149360 A1 | 7/2006 | Schwammenthal et al. |
| 2006/0154230 A1 | 7/2006 | Cunanan et al. |
| 2006/0161249 A1 | 7/2006 | Realyvasquez et al. |
| 2006/0167543 A1 | 7/2006 | Bailey et al. |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0229708 A1 | 10/2006 | Powell et al. |
| 2006/0235508 A1 | 10/2006 | Lane et al. |
| 2006/0241745 A1 | 10/2006 | Solem |
| 2006/0246888 A1 | 11/2006 | Bender et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0259137 A1* | 11/2006 | Artof et al. .................. 623/2.18 |
| 2006/0265056 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1* | 12/2006 | Rowe et al. .................. 623/2.11 |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244558 A1 | 10/2007 | Machiraju |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0021546 A1 | 1/2008 | Patz et al. |
| 2008/0033543 A1 | 2/2008 | Gurskis et al. |
| 2008/0065198 A1 | 3/2008 | Quintessenza |
| 2008/0082161 A1 | 4/2008 | Woo |
| 2008/0119875 A1 | 5/2008 | Ino et al. |
| 2008/0281411 A1 | 11/2008 | Berreklouw |
| 2008/0319543 A1 | 12/2008 | Lane |
| 2009/0036903 A1 | 2/2009 | Ino et al. |
| 2009/0192599 A1 | 7/2009 | Lane et al. |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |
| 2010/0161036 A1 | 6/2010 | Pintor et al. |
| 2010/0292784 A1 | 11/2010 | Giannetti et al. |
| 2010/0331972 A1 | 12/2010 | Pintor et al. |
| 2011/0147251 A1 | 6/2011 | Hodshon et al. |
| 2012/0065729 A1 | 3/2012 | Pintor et al. |

FOREIGN PATENT DOCUMENTS

| | | |
|---|---|---|
| EP | 0096721 A1 | 12/1983 |
| EP | 0125393 A1 | 11/1984 |
| EP | 0143246 A2 | 6/1985 |
| EP | 0179562 A1 | 4/1986 |
| EP | 1171059 A1 | 1/2002 |
| GB | 2056023 A | 3/1981 |
| GB | 2069843 A | 9/1981 |
| GB | 2254254 A | 10/1992 |
| GB | 2279134 A | 12/1994 |
| SU | 116573 A1 | 7/1985 |
| SU | 1697790 A1 | 12/1991 |
| WO | 8900840 A1 | 2/1989 |
| WO | 9115167 A1 | 10/1991 |
| WO | 9212690 A1 | 8/1992 |
| WO | 9213502 A1 | 8/1992 |
| WO | 9219184 A1 | 11/1992 |
| WO | 9219185 A1 | 11/1992 |
| WO | 9517139 A1 | 6/1995 |
| WO | 9528899 A1 | 11/1995 |
| WO | 9640006 A1 | 12/1996 |
| WO | 9709933 A1 | 3/1997 |
| WO | 9709944 A1 | 3/1997 |
| WO | 9724871 A2 | 7/1997 |
| WO | 9727799 A1 | 8/1997 |
| WO | 9741801 A1 | 11/1997 |
| WO | 9742871 A1 | 11/1997 |
| WO | 9806329 A1 | 2/1998 |
| WO | 9911201 A2 | 3/1999 |
| WO | 9915112 A1 | 4/1999 |
| WO | 9951169 A1 | 10/1999 |
| WO | 0032105 A1 | 6/2000 |
| WO | 0040176 A1 | 7/2000 |
| WO | 0060995 A2 | 10/2000 |
| WO | 0154624 A1 | 8/2001 |
| WO | 0154625 A1 | 8/2001 |
| WO | 02076347 | 10/2002 |
| WO | 2006086135 A2 | 8/2006 |

OTHER PUBLICATIONS

Sadowski, Jerzy; Kapelak, Boguslaw; Bartus, Krzysztof, "Sutureless Heart Valve Implantation—A Case Study," Touch Briefings, 2005, pp. 48-50.

* cited by examiner

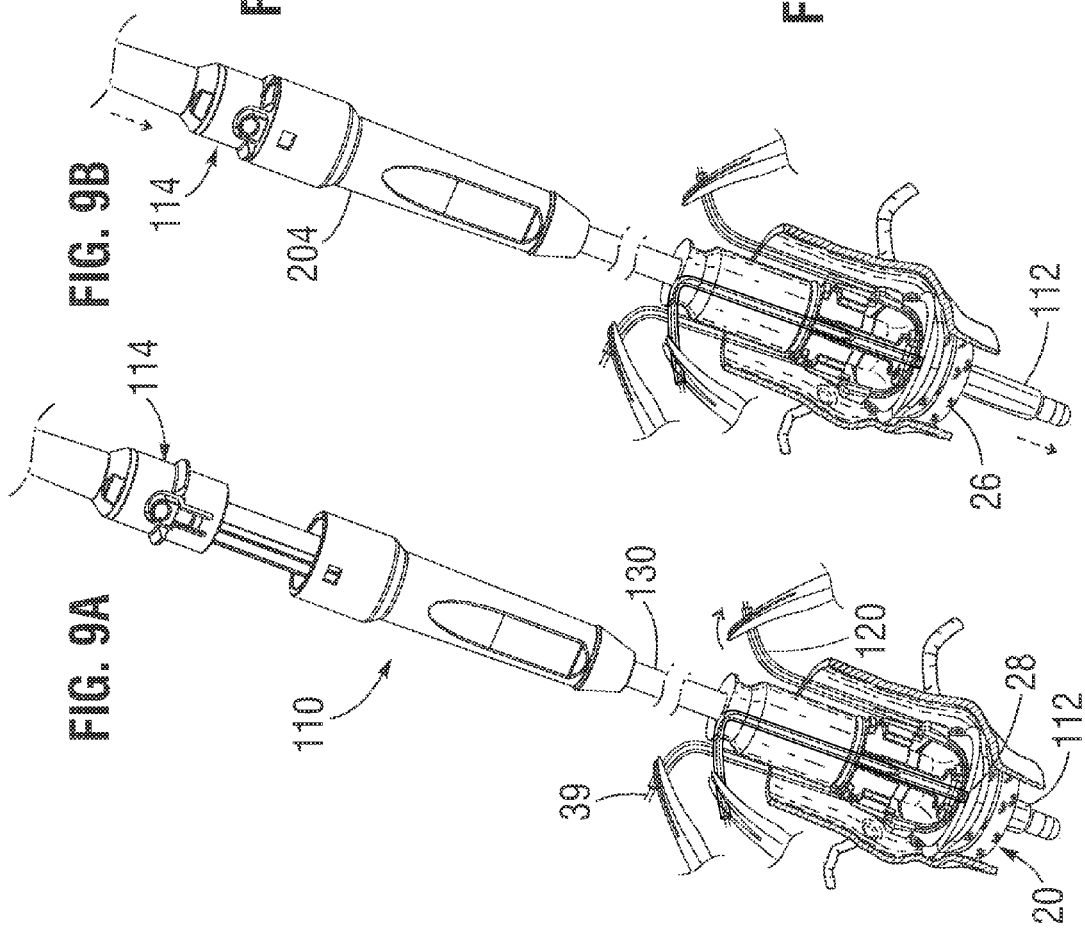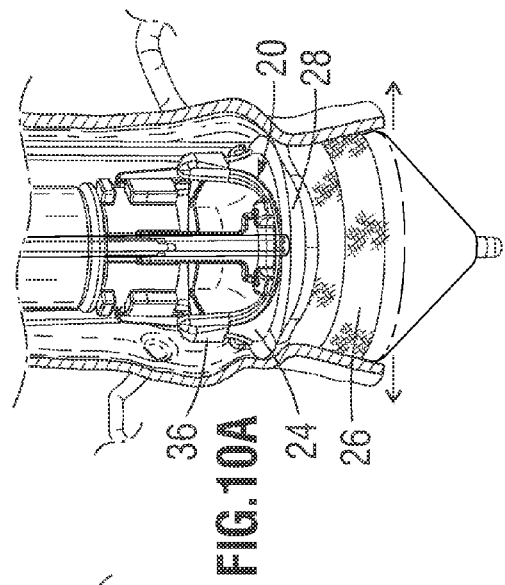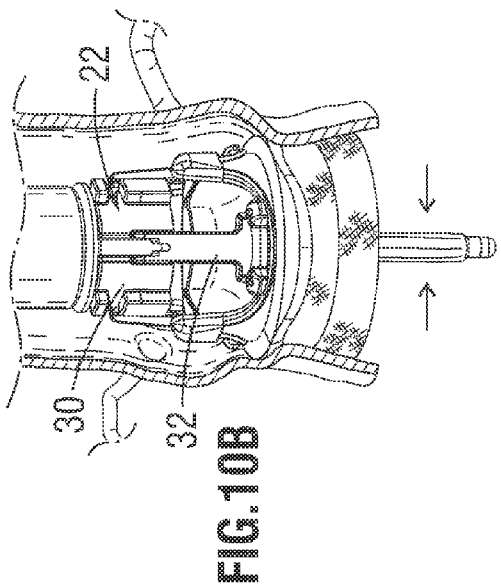

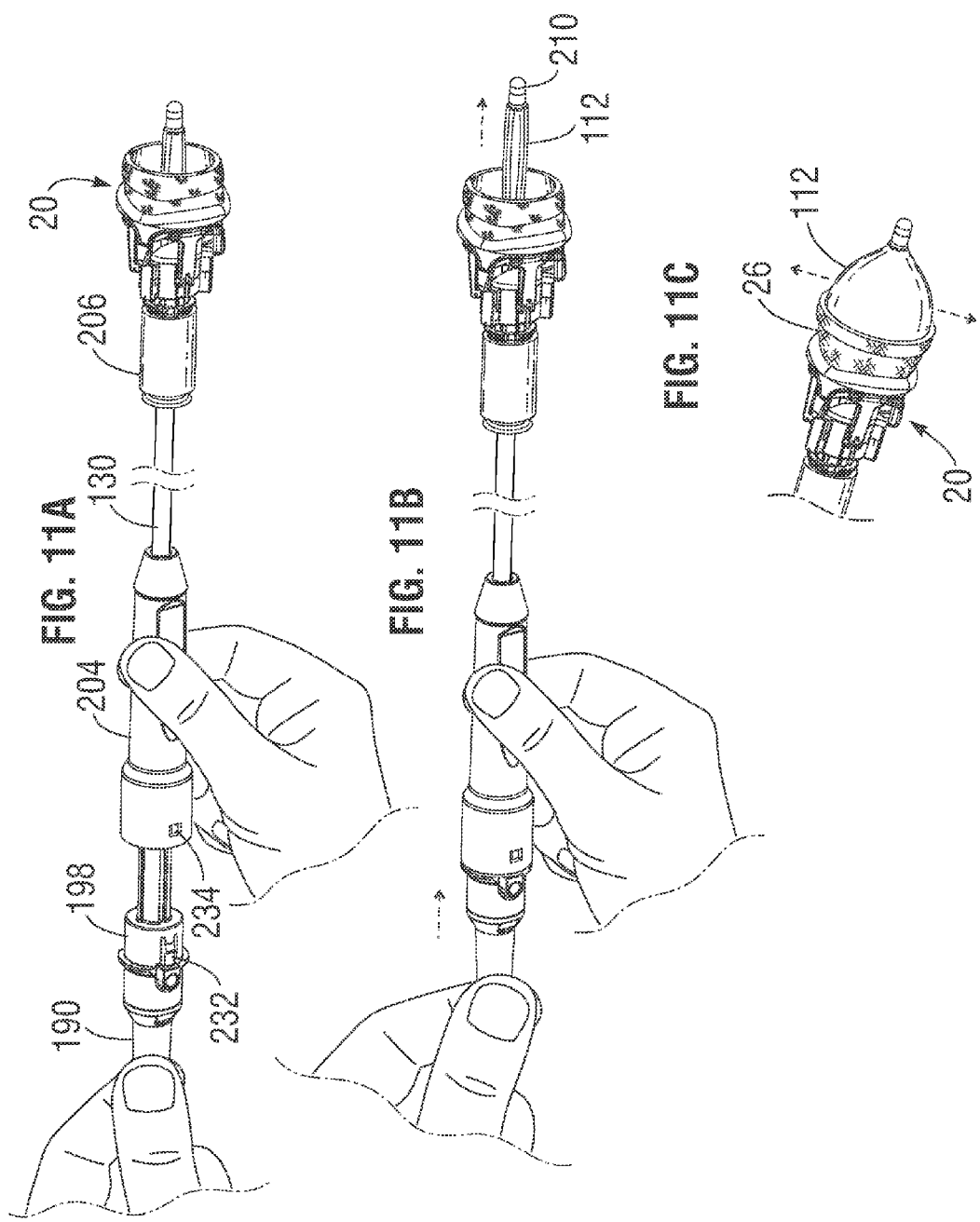

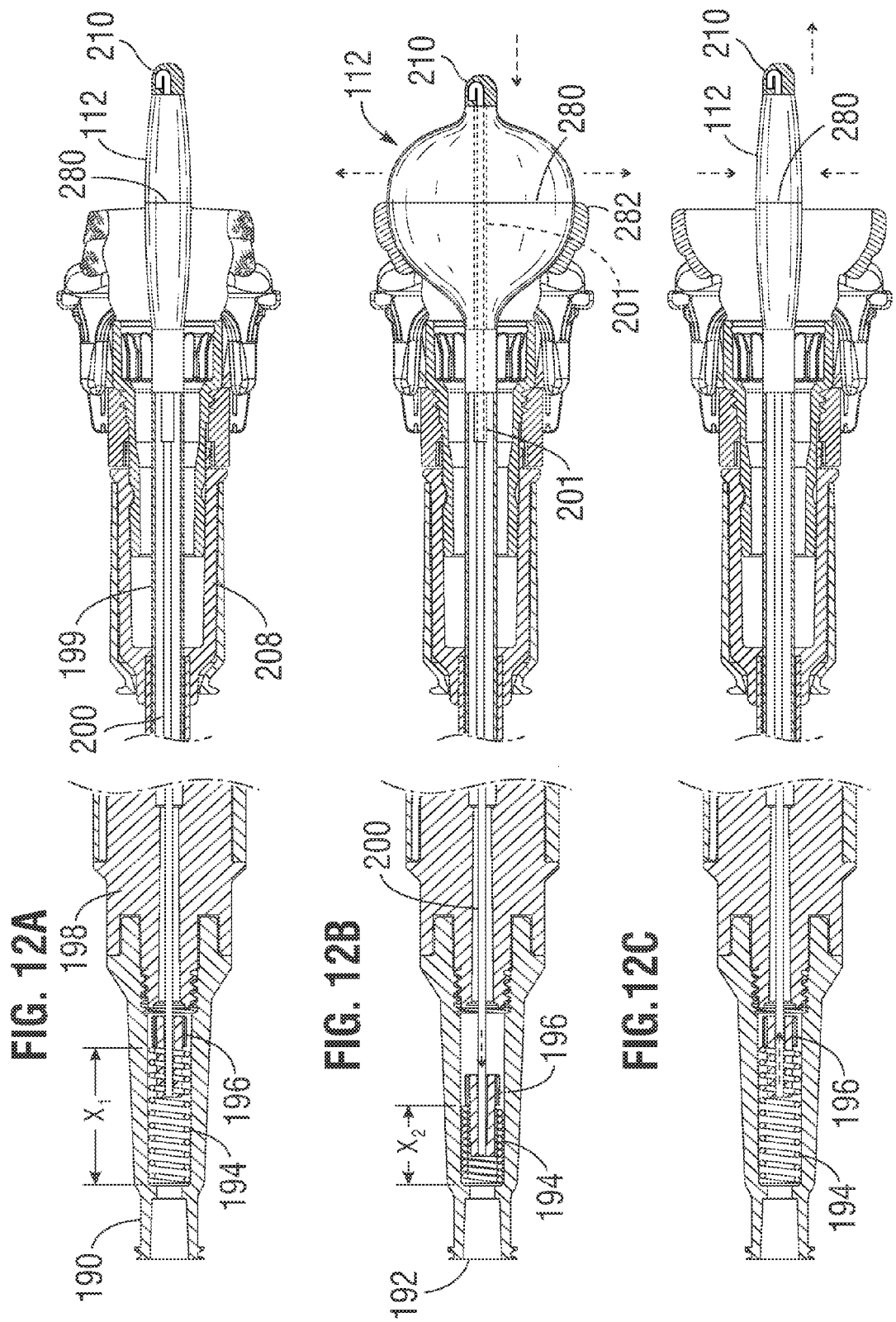

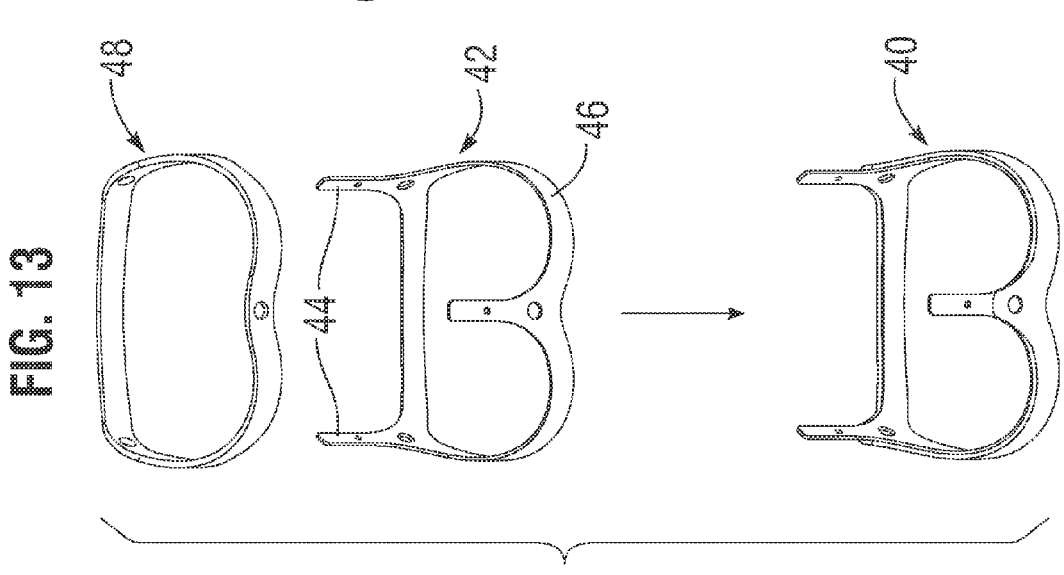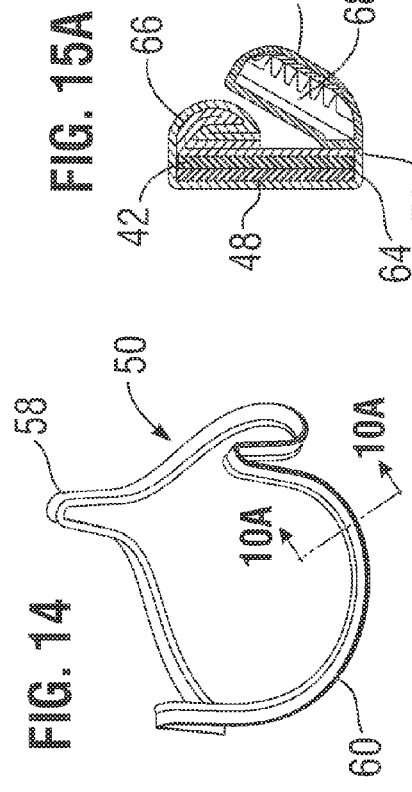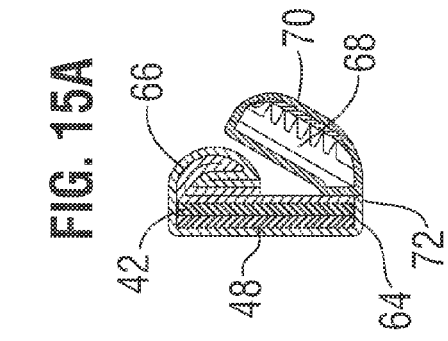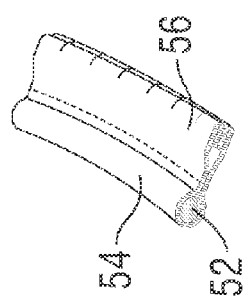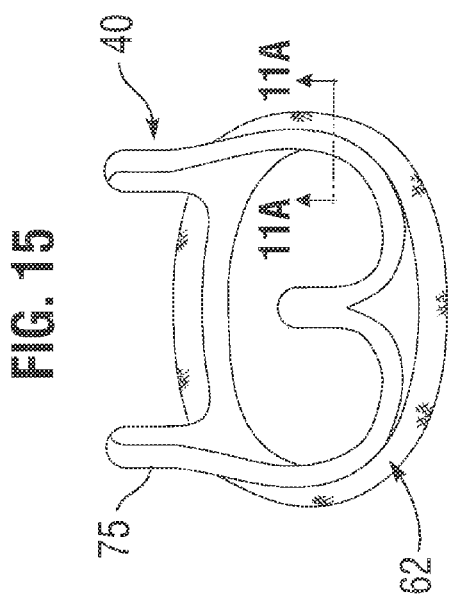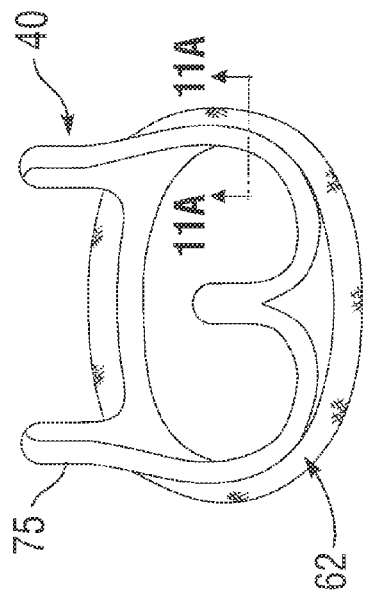

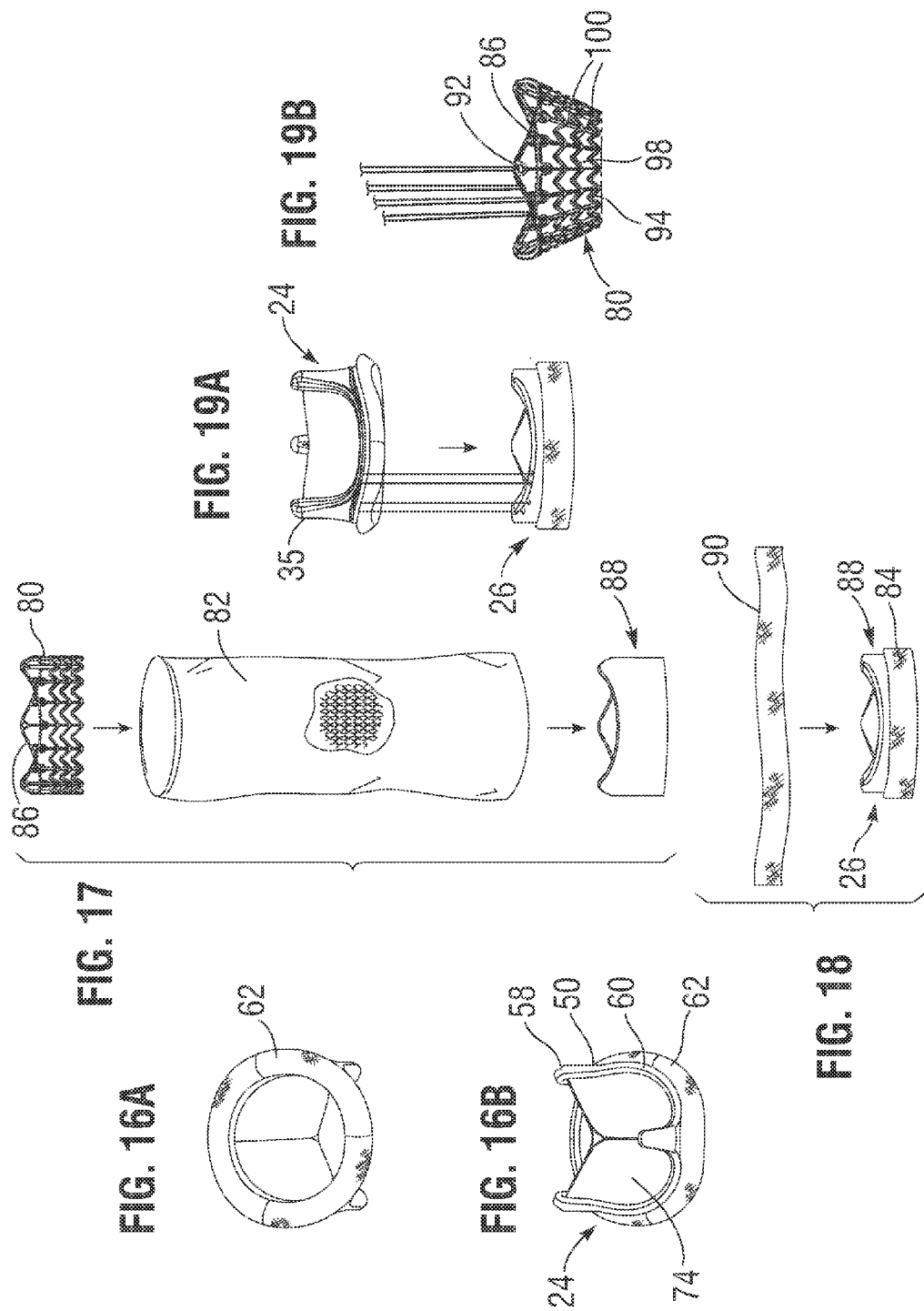

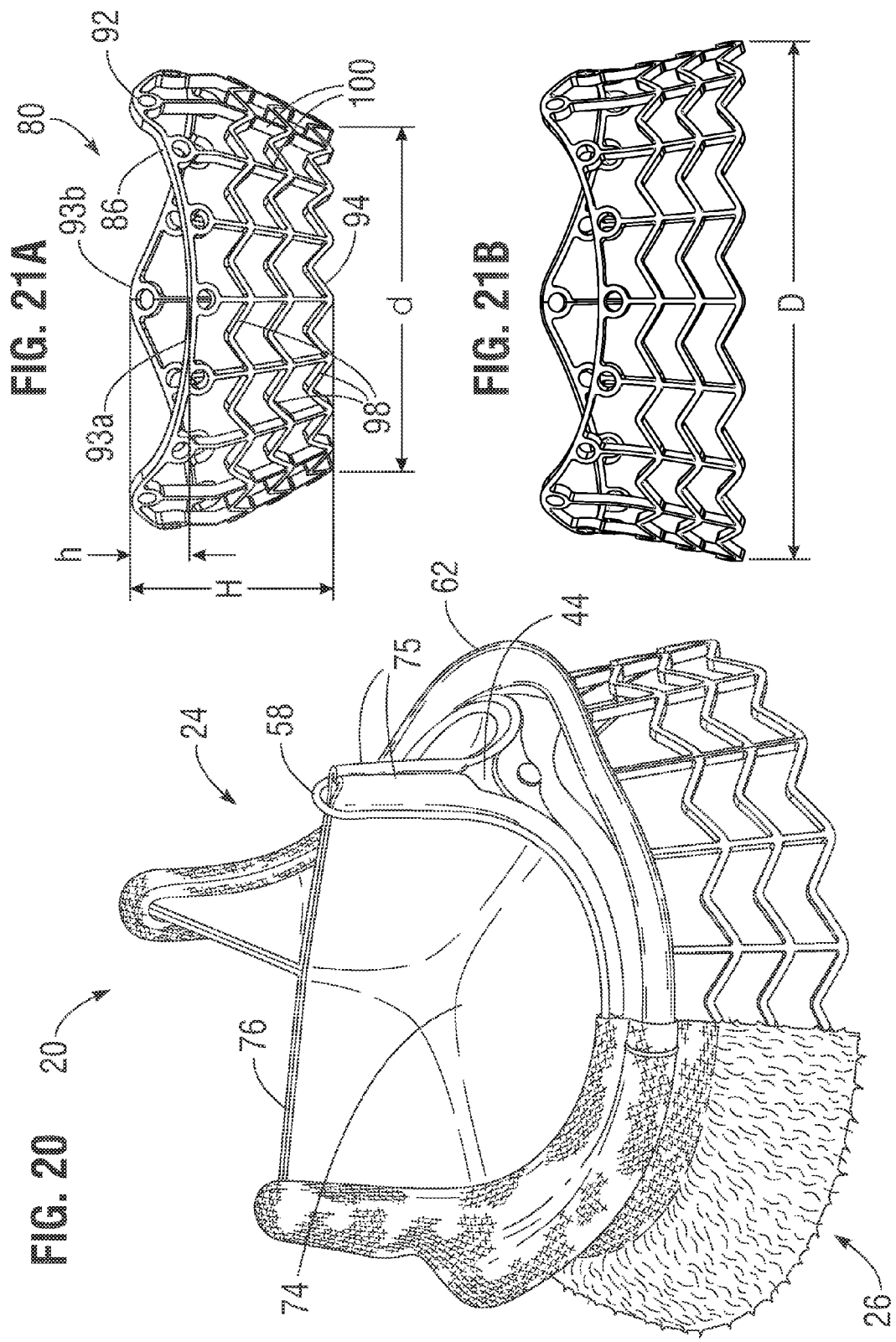

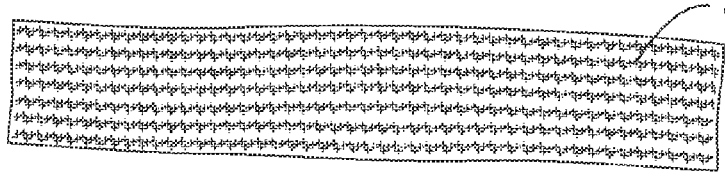
FIG. 27A
FIG. 27B
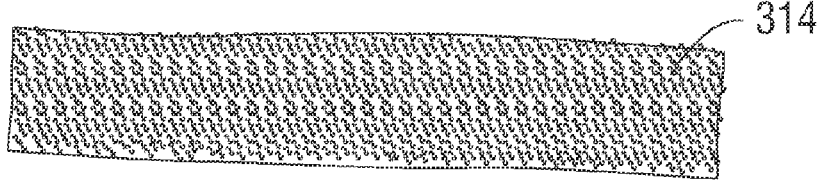
FIG. 28
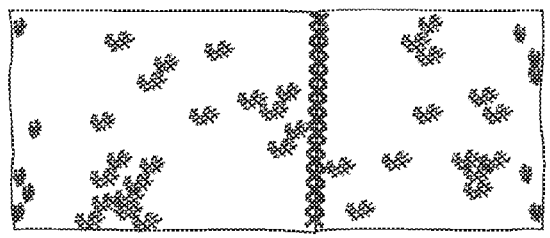
FIG. 29A
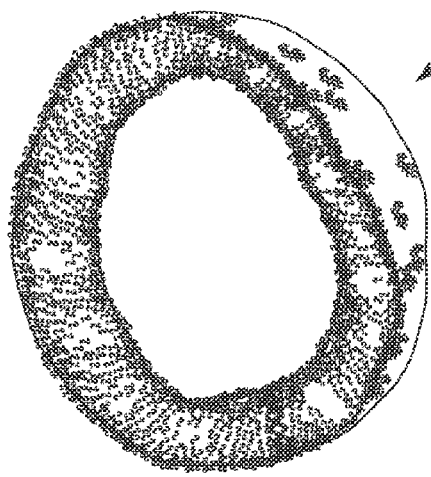
FIG. 29B
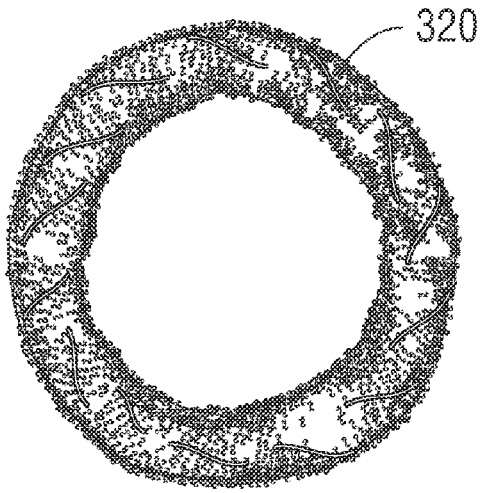
FIG. 29C

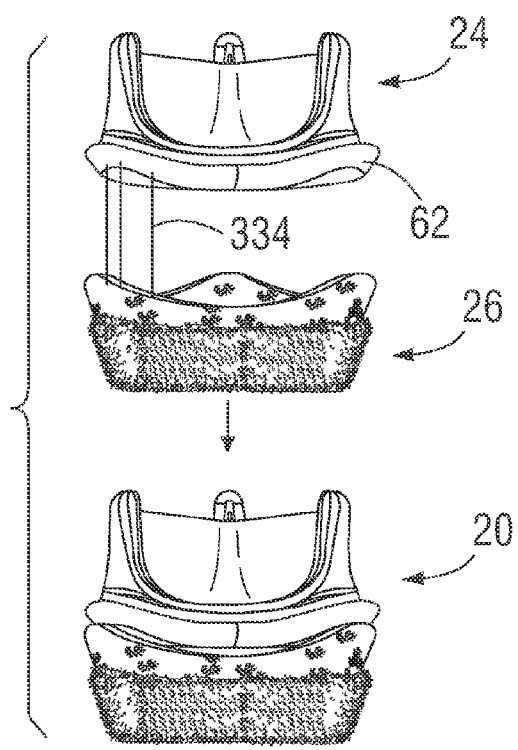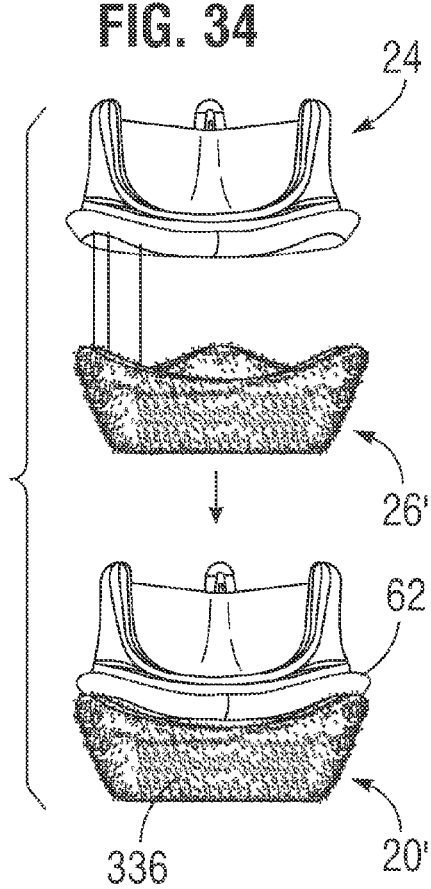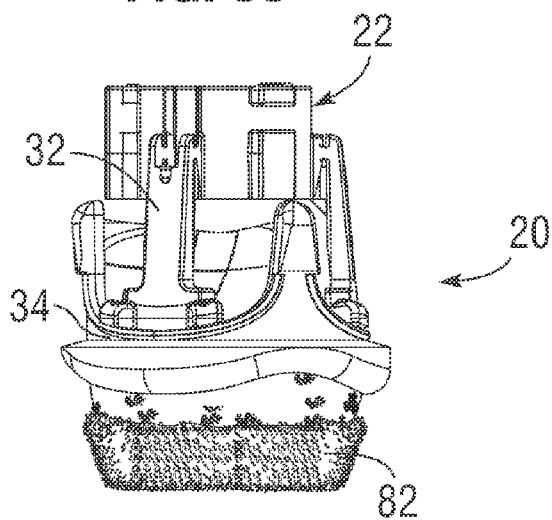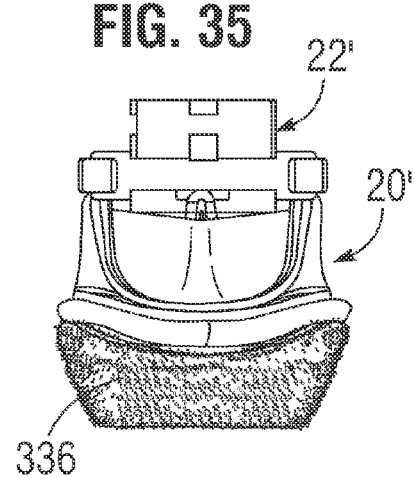

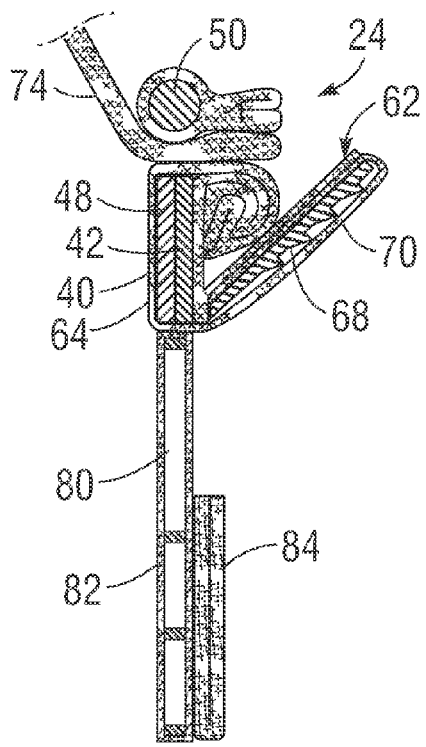
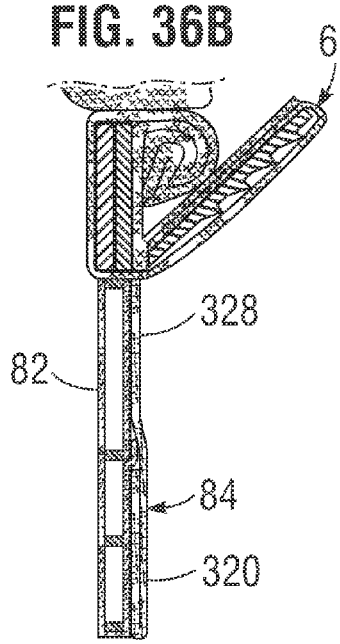
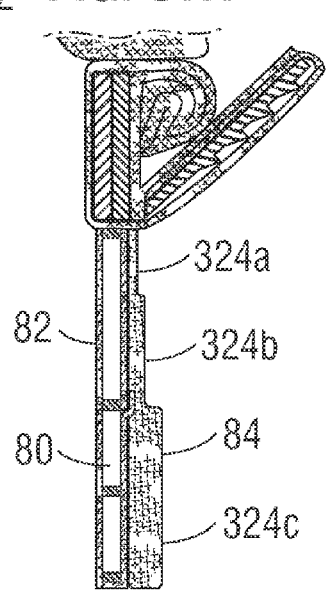
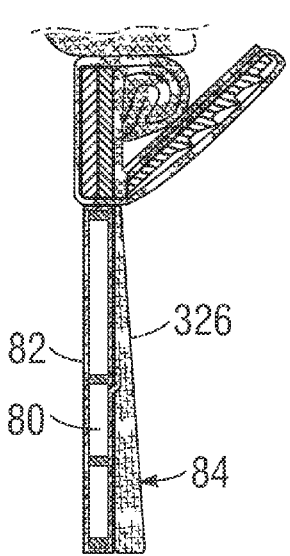
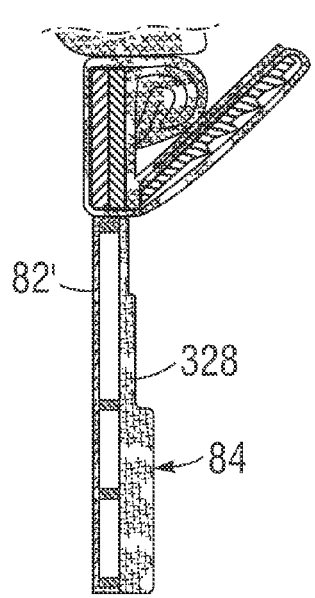
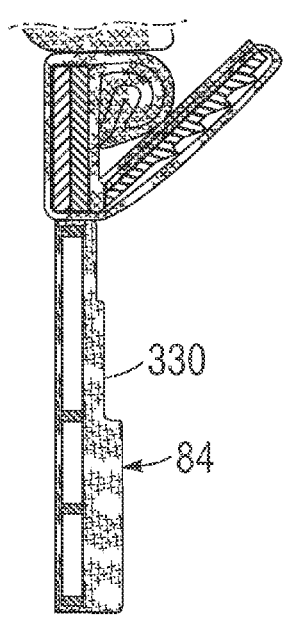

FIG. 39D  FIG. 39E  FIG. 39F  FIG. 39G
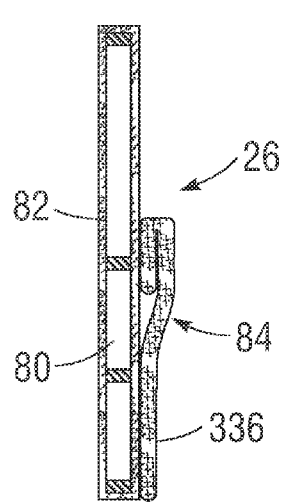
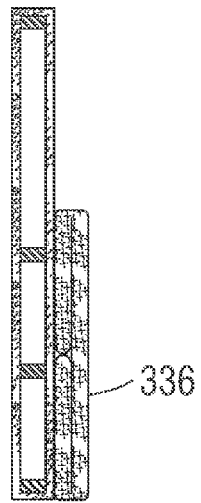
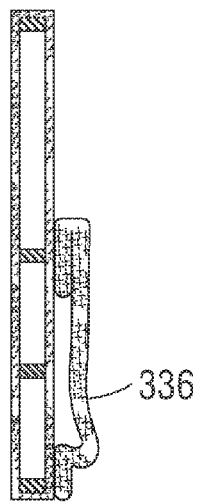
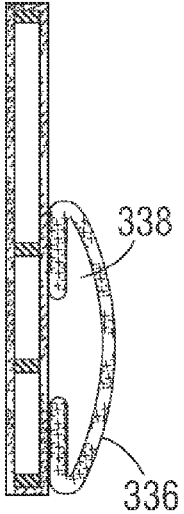
FIG. 39H  FIG. 39I  FIG. 39J
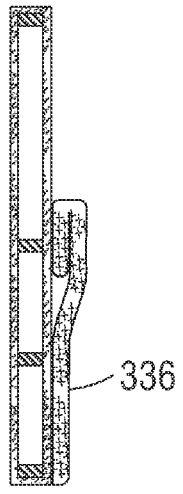
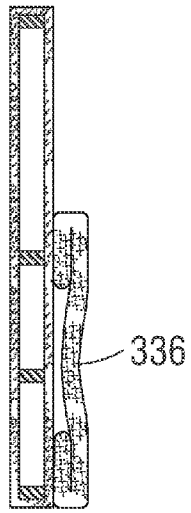
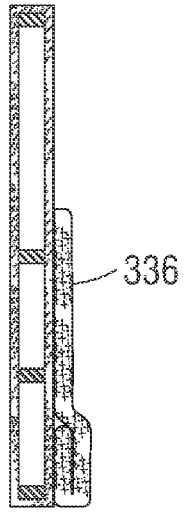

RAPIDLY DEPLOYABLE SURGICAL HEART VALVES

RELATED APPLICATIONS

The present application is a continuation-in-part of U.S. patent application Ser. No. 13/167,639, filed Jun. 23, 2011, which claims priority under 35 U.S.C. §119(e) to U.S. provisional application No. 61/381,931 filed Sep. 10, 2010.

FIELD OF THE INVENTION

The present invention generally relates to prosthetic valves for implantation in body channels. More particularly, the present invention relates to unitary surgical prosthetic heart valves configured to be surgically implanted in less time than current valves, and associated valve delivery systems.

BACKGROUND OF THE INVENTION

In vertebrate animals, the heart is a hollow muscular organ having four pumping chambers as seen in FIG. 1—the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice.

The atria are the blood-receiving chambers, which pump blood into the ventricles. The ventricles are the blood-discharging chambers. A wall composed of fibrous and muscular parts, called the interatrial septum separates the right and left atria (see FIGS. 2 to 4). The fibrous interatrial septum is a materially stronger tissue structure compared to the more friable muscle tissue of the heart. An anatomic landmark on the interatrial septum is an oval, thumbprint sized depression called the oval fossa, or fossa ovalis (shown in FIG. 4).

The synchronous pumping actions of the left and right sides of the heart constitute the cardiac cycle. The cycle begins with a period of ventricular relaxation, called ventricular diastole. The cycle ends with a period of ventricular contraction, called ventricular systole. The four valves (see FIGS. 2 and 3) ensure that blood does not flow in the wrong direction during the cardiac cycle; that is, to ensure that the blood does not back flow from the ventricles into the corresponding atria, or back flow from the arteries into the corresponding ventricles. The mitral valve is between the left atrium and the left ventricle, the tricuspid valve between the right atrium and the right ventricle, the pulmonary valve is at the opening of the pulmonary artery, and the aortic valve is at the opening of the aorta.

FIGS. 2 and 3 show the anterior (A) portion of the mitral valve annulus abutting the non-coronary leaflet of the aortic valve. The mitral valve annulus is in the vicinity of the circumflex branch of the left coronary artery, and the posterior (P) side is near the coronary sinus and its tributaries.

Various surgical techniques may be used to repair a diseased or damaged valve. In a valve replacement operation, the damaged leaflets are excised and the annulus sculpted to receive a replacement valve. Due to aortic stenosis and other heart valve diseases, thousands of patients undergo surgery each year wherein the defective native heart valve is replaced by a prosthetic valve, either bioprosthetic or mechanical. Another less drastic method for treating defective valves is through repair or reconstruction, which is typically used on minimally calcified valves. The problem with surgical therapy is the significant insult it imposes on these chronically ill patients with high morbidity and mortality rates associated with surgical repair.

When the valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective valves are deemed inoperable because their condition is too frail to withstand the procedure. By some estimates, about 30 to 50% of the subjects suffering from aortic stenosis who are older than 80 years cannot be operated on for aortic valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. No. 5,411,552 to Andersen et al. describes a collapsible valve percutaneously introduced in a compressed state through a catheter and expanded in the desired position by balloon inflation. Although these remote implantation techniques have shown great promise for treating certain patients, replacing a valve via surgical intervention is still the preferred treatment procedure. One hurdle to the acceptance of remote implantation is resistance from doctors who are understandably anxious about converting from an effective, if imperfect, regimen to a novel approach that promises great outcomes but is relatively foreign. In conjunction with the understandable caution exercised by surgeons in switching to new techniques of heart valve replacement, regulatory bodies around the world are moving slowly as well. Numerous successful clinical trials and follow-up studies are in process, but much more experience with these new technologies will be required before they are completely accepted.

Accordingly, there is a need for an improved device and associated method of use wherein a prosthetic valve can be surgically implanted in a body channel in a more efficient procedure that reduces the time required on extracorporeal circulation. It is desirable that such a device and method be capable of helping patients with defective valves that are deemed inoperable because their condition is too frail to withstand a lengthy conventional surgical procedure.

Furthermore, surgeons relate that one of the most difficult tasks when attempting minimally invasive heart valve implantation or implantation through a small incision is tying the suture knots that hold the valve in position. A typical aortic valve implant utilizes 12-24 sutures (commonly 15) distributed evenly around and manually tied on one side of the sewing ring. The knots directly behind the commissure posts of a prosthetic aortic valve are particularly challenging because of space constraints. Eliminating the need to tie suture knots or even reducing the number of knots to those that are more accessible would greatly facilitate the use of smaller incisions that reduces infection risk, reduces the need for blood transfusions and allows more rapid recovery compared to patients whose valves are implanted through the full sternotomy commonly used for heart valve implantation.

The present invention addresses these needs and others.

SUMMARY OF THE INVENTION

Various embodiments of the present application provide prosthetic valves and methods of use for replacing a defective native valve in a human heart. Certain embodiments are particularly well adapted for use in a surgical procedure for quickly and easily replacing a heart valve while minimizing time using extracorporeal circulation (i.e., bypass pump).

In one embodiment, a method for treating a native aortic valve in a human heart to replace the function of the aortic valve, comprises: 1) accessing a native valve through an opening in a chest; 2) placing guiding sutures in the annulus 3) advancing a heart valve within a lumen of the annulus; and 4) plastically expanding a metallic anchoring skirt on the heart valve to mechanically couple to the annulus in a quick and efficient manner.

The native valve leaflets may be removed before delivering the prosthetic valve. Alternatively, the native leaflets may be left in place to reduce surgery time and to provide a stable base for fixing the anchoring skirt within the native valve. In one advantage of this method, the native leaflets recoil inward to enhance the fixation of the metallic anchoring skirt in the body channel. When the native leaflets are left in place, a balloon or other expansion member may be used to push the valve leaflets out of the way and thereby dilate the native valve before implantation of the anchoring skirt. The native annulus may be dilated between 1.0-5 mm from their initial orifice size to accommodate a larger sized prosthetic valve.

In accordance with a preferred aspect, a heart valve includes a prosthetic valve defining therein a non-expandable, non-collapsible orifice, and an expandable anchoring skirt extending from an inflow end thereof. The anchoring skirt has a contracted state for delivery to an implant position and an expanded state configured for outward connection to the surrounding annulus. Desirably, the anchoring skirt is plastically expandable.

In one preferred form, a prosthetic heart valve for implant at a heart valve annulus comprise a non-expandable, non-collapsible annular support structure defining a flow orifice and having an inflow end. Valve leaflets attach to the support structure and are mount to alternately open and close across the flow orifice. A plastically-expandable stent frame has a first end extending around the flow orifice and connected to the valve at the inflow end of the support structure. The stent frame has a second end projecting in the inflow direction away from the support structure and is capable of assuming a contracted state for delivery to an implant position and a wider expanded state for outward contact with an annulus. The stent frame has an undulating first end with peaks and valleys that conform to a similar shape of the inflow end of the support structure, and the stent frame in the contracted state extends away from the inflow end of the support structure in a tubular portion between the peaks and valleys and then angles inward in a conical portion to the second end. In one embodiment, the stent frame angles inward in a conical portion in the contracted state and the second end defines an orifice that is non-circular, such as by non-uniform crimping.

In another aspect, a prosthetic heart valve for implant at a heart valve annulus, comprises:

a. a non-expandable, non-collapsible annular support structure defining a flow orifice and having an inflow end;
b. valve leaflets attached to the support structure and mounted to alternately open and close across the flow orifice;
c. a plastically-expandable stent frame having a first end extending around the flow orifice and connected to the valve at the inflow end of the support structure, the stent frame having a second end projecting in the inflow direction away from the support structure and being capable of assuming a contracted state for delivery to an implant position and a wider expanded state for outward contact with an annulus; and
d. a fabric covering around the stent frame including an enlarged sealing flange surrounding the second end.

Preferably, the support structure includes a plurality of commissure posts projecting in an outflow direction, and the valve leaflets are flexible and attached to the support structure and commissure posts and mounted to alternately open and close across the flow orifice. Also, a sealing ring desirably circumscribes an inflow end of the support structure. The enlarged sealing flange surrounding the second end of the plastically-expandable stent frame is spaced from the suture permeable ring to help conform the stent frame to the aortic annulus.

In one embodiment, the heart valve comprises a commercially available prosthetic valve having a sewing ring, and the anchoring skirt attaches to the sewing ring. The contracted state of the anchoring skirt may be conical, tapering inward from the first end toward the second end, while in the expanded state the stent frame is conical but tapering outward from the first end toward the second end. The anchoring skirt preferably comprises a plurality of radially expandable struts at least some of which are arranged in rows, wherein the distalmost row has the greatest capacity for expansion from the contracted state to the expanded state. The sewing ring may comprise a solid yet compressible material that is relatively stiff so as to provide a seal against the annulus and has a concave inflow shape that conforms to the annulus.

A method of delivery and implant of a prosthetic heart valve system is also disclosed herein, comprising the steps of:

a. providing a heart valve including a prosthetic valve having an expandable stent frame, the stent frame having a contracted state for delivery to an implant position and an expanded state configured for outward connection to the annulus, the heart valve being mounted on a holder having a proximal hub and lumen therethrough, the proximal hub connected to the distal end of a handle shaft having a lumen therethrough,
b. advancing the heart valve with the stent frame in its contracted state to an implant position adjacent the annulus;
c. passing a first balloon catheter through the lumens of the handle shaft and the holder and within the heart valve, and inflating a balloon on the first balloon catheter;
d. deflating the balloon and retracting the first balloon catheter from within the heart valve, and removing the first balloon catheter from the handle shaft;
e. inserting a second balloon catheter into the handle shaft and passing the second balloon catheter through the lumens of the handle shaft and the holder to within the heart valve, and inflating a balloon on the second balloon catheter to expand the stent frame.

The method may involve increasing the orifice size of the heart valve annulus by 1.0-5.0 mm by plastically expanding the stent frame. In one embodiment, the prosthetic valve of the valve component is selected to have an orifice size that matches the increased orifice size of the heart valve annulus.

One embodiment of the method further includes mounting the heart valve on a holder having a proximal hub and lumen therethrough. The holder mounts on the distal end of a handle shaft having a lumen therethrough, and the method includes passing a balloon catheter through the lumen of the handle shaft and the holder and within the heart valve, and inflating a balloon on the balloon catheter to expand the anchoring skirt. The heart valve mounted on the holder may be packaged separately from the handle shaft and the balloon catheter. Desirably, the contracted state of the expandable stent frame/anchoring skirt is conical, and the balloon on the balloon catheter has a larger distal expanded end than its proximal expanded end so as to apply expansion deflection to the anchoring skirt and not to the prosthetic valve. In a preferred embodiment, the balloon distal and proximal diameters are essentially the same, the balloon being generally symmetric across an axial midline, and the balloon midline is positioned near the distal end of the stent frame prior to inflation. The delivery system including the valve holder is designed to position the balloon within the heart valve so that it inflates within the anchoring skirt, and not within the actual valve components.

Preferably, a valve delivery system includes an integrated balloon catheter and tubular handle shaft through which the catheter extends. A distal end of the handle shaft includes an adapter which mates with a holder of the heart valve, and a locking sleeve for rapidly connecting the delivery system to the heart valve holder. A balloon of the balloon catheter resides within the adapter and may be advanced distally into position for expanding the anchoring skirt. A tubular balloon introducer sleeve attached when removing the heart valve from a storage jar facilitates passage of the balloon through the heart valve.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIG. 9A is a perspective cutaway view of an aortic annulus showing a portion of the adjacent left ventricle below the ascending aorta, illustrating an exemplary hybrid heart valve mounted on a distal section of a delivery handle advanced into position within the aortic annulus along guide sutures;

FIG. 9B is a view similar to FIG. 9A illustrating advancement of a balloon catheter through the heart valve into position to expand an anchoring skirt thereon;

FIG. 10A is an enlarged view of the aortic valve implant site showing the balloon of the balloon catheter inflated to expand the anchoring skirt, while FIG. 10B shows the balloon deflated and stretched;

FIGS. 11A-11C are perspective views illustrating deployment of the balloon catheter through the prosthetic heart valve and expansion of the balloon to expand the anchoring skirt, analogous to FIGS. 9A-10A;

FIG. 12A is a partial sectional view of the heart valve delivery system having the prosthetic heart valve and valve holder thereon and in the balloon advanced configuration of FIG. 11B;

FIG. 12B is a partial sectional view similar to FIG. 12A and showing movement of a balloon extension wire to compress a spring upon balloon inflation;

FIG. 12C is similar to FIG. 12A and shows return movement of the balloon extension wire and spring upon balloon deflation;

FIG. 13 is an exploded view of an inner structural band subassembly of the exemplary prosthetic heart valve;

FIG. 14 is a perspective view of a further valve subassembly of an undulating cloth-covered wireform, and FIG. 14A is a detailed sectional view of a cusp portion thereof;

FIG. 15 is a perspective view of the band subassembly and a suture-permeable sewing ring joined together, and FIG. 15A is a radial sectional view through a cusp portion thereof;

FIGS. 16A and 16B are inflow and outflow perspective views, respectively, of a surgical heart valve before coupling with an inflow anchoring skirt to form the prosthetic heart valve of the present application;

FIG. 17 is an exploded assembly view of a portion of a cloth-covered anchoring skirt for coupling to the surgical heart valve;

FIG. 18 is an exploded assembly view of the portion of the cloth-covered anchoring skirt shown in FIG. 17 and a lower sealing flange secured thereto to form the inflow anchoring skirt;

FIG. 19A shows the surgical heart valve above the cloth-covered anchoring skirt and schematically shows one method of coupling the two elements, while FIG. 19B illustrates an inner plastically-expandable stent frame of the anchoring skirt and the pattern of coupling sutures passed therethrough;

FIG. 20 is a partially cutaway perspective view of an assembled prosthetic heart valve as disclosed herein;

FIGS. 21A and 21B are elevational views of an exemplary anchoring skirt shown in both radially contracted and expanded states, respectively;

FIG. 26A shows an intermediate step in covering the anchoring skirt of FIG. 25 with fabric, while

FIGS. 27A-27B are plan views of opposite sides of a strip of plush fabric used to create a sealing flange on the expandable anchoring skirt as disclosed herein;

FIG. 28 shows a single layer of the strip of fabric sewn into a ring;

FIGS. 29A-29C show several steps in folding and sewing the ring of fabric from FIG. 28 into a double-layer sealing flange;

FIG. 32 schematically illustrates the coupling of a tissue valve member with the anchoring skirt assembly of FIG. 31C, and FIG. 33 shows attachment of an exemplary valve holder thereto;

FIG. 34 schematically illustrates the coupling of a tissue valve member with an alternative anchoring skirt assembly, and FIG. 35 shows attachment of an alternative valve holder thereto;

FIGS. 36A-36B are radial cross-sections parallel to the axis of an exemplary heart valve showing construction of an exemplary cloth covering of an anchoring skirt, with the anchoring skirt schematically shown tubular for simplicity;

FIGS. 37A-37D are radial cross-sections similar to FIGS. 36A-36B showing an alternative cloth covering with a sealing flange that becomes gradually thicker away from the valve member;

FIGS. 39A-39J are radial cross-sections of a schematic tubular anchoring skirt with a cloth-covering having different folded sealing flanges;

DETAILED DESCRIPTION OF THE PREFERRED EMBODIMENTS

Figure 1:
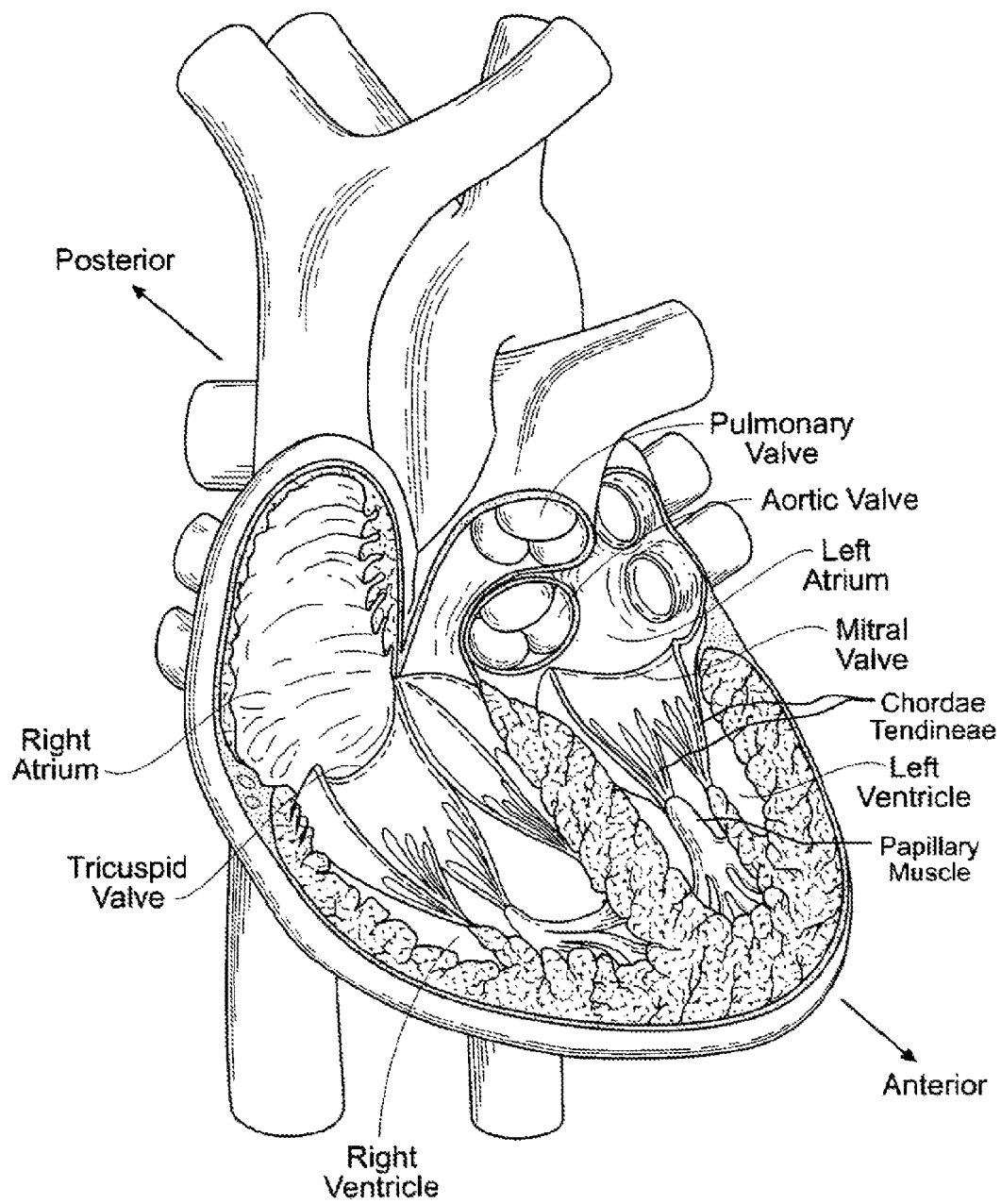
FIG. 1 is an anatomic anterior view of a human heart, with portions broken away and in section to view the interior heart chambers and adjacent structures.
Figure 2:
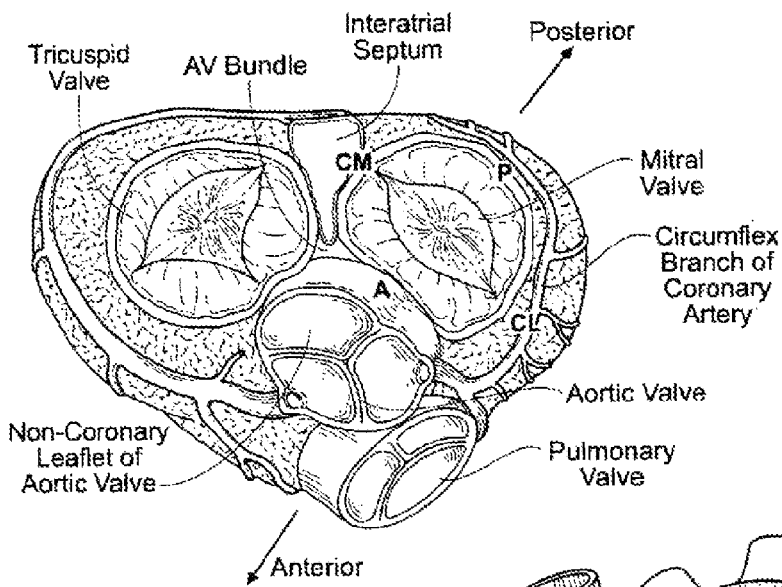
FIG. 2 is an anatomic superior view of a section of the human heart showing the tricuspid valve in the right atrium, the mitral valve in the left atrium, and the aortic valve in between, with the tricuspid and mitral valves open and the aortic and pulmonary valves closed during ventricular diastole (ventricular filling) of the cardiac cycle.

The present invention attempts to overcome drawbacks associated with conventional, open-heart surgery, while also adopting some of the techniques of newer technologies which decrease the duration of the treatment procedure. The prosthetic heart valves of the present invention are primarily intended to be delivered and implanted using conventional surgical techniques, including the aforementioned open-heart surgery. There are a number of approaches in such surgeries, all of which result in the formation of a direct access pathway to the particular heart valve annulus. For clarification, a direct access pathway is one that permits direct (i.e., naked eye) visualization of the heart valve annulus. In addition, it will be recognized that embodiments of the prosthetic heart valves described herein may also be configured for delivery using percutaneous approaches, and those minimally-invasive surgical approaches that require remote implantation of the valve using indirect visualization. However, the latter two approaches—percutaneous and minimally-invasive—invariably rely on collapsible/expandable valve constructs. And, while certain aspects described herein could be useful for such valves and techniques, the primary focus and main advantages of the present application is in the realm of non-expandable "surgical" valves introduced in conventional manners.

One primary aspect of the present invention is a "unitary" prosthetic heart valve in which a tissue anchor is implanted at the same time as a valve member resulting in certain advantages. The exemplary unitary prosthetic heart valve of the present invention is a hybrid valve member, if you will, with both non-expandable and expandable portions. By utilizing an expandable anchoring skirt or stent coupled to a non-expandable valve member, the duration of the anchoring operation is greatly reduced as compared with a conventional sewing procedure utilizing an array of sutures. The expandable anchoring skirt may simply be radially expanded outward into contact with the implantation site, or may be provided with additional anchoring means, such as barbs. As stated, conventional open-heart approach and cardiopulmonary bypass familiar to cardiac surgeons are used. However, due to the expandable anchoring skirt, the time on bypass is greatly reduced by the relative speed of implant in contrast to the previous time-consuming knot-tying process.

For definitional purposes, the terms "stent" or "coupling stent" refer to a structural component that is capable of anchoring to tissue of a heart valve annulus. The coupling stents described herein are most typically tubular stents, or stents having varying shapes or diameters. A stent is normally formed of a biocompatible metal frame, such as stainless steel or Nitinol. More preferably, in the context of the present invention the stents are made from laser-cut tubing of a plastically-expandable metal. Other coupling stents that could be used with valves of the present invention include rigid rings, spirally-wound tubes, and other such tubes that fit tightly within a valve annulus and define an orifice therethrough for the passage of blood. It is entirely conceivable, however, that the coupling stent could be separate clamps or hooks that do not define a continuous periphery. Although such devices sacrifice some contact uniformity, and speed and ease of deployment, they could be configured to work in conjunction with a particular valve member.

A distinction between self-expanding and balloon-expanding stents exists in the field. A self-expanding stent may be crimped or otherwise compressed into a small tube and possesses sufficient elasticity to spring outward by itself when a restraint such as an outer sheath is removed. In contrast, a balloon-expanding stent is made of a material that is substantially less elastic, and indeed must be plastically expanded from the inside out when converting from a contracted to an expanded diameter. It should be understood that the term balloon-expanding stents encompasses plastically-expandable stents, whether or not a balloon is used to actually expand it (e.g., a device with mechanical fingers could expand the stent). The material of the stent plastically deforms after application of a deformation force such as an inflating balloon or expanding mechanical fingers. Consequently, the term "balloon-expandable stent" should be understood as referring to the material or type of the stent as opposed to the specific expansion means.

The term "valve member" refers to that component of a heart valve that possesses the fluid occluding surfaces to prevent blood flow in one direction while permitting it in another. As mentioned above, various constructions of valve members are available, including those with flexible leaflets and those with rigid leaflets, or even a ball and cage arrangement. The leaflets may be bioprosthetic, synthetic, metallic, or other suitable expedients. In a preferred embodiment, the non-expandable valve member is an "off-the-shelf" standard surgical valve of the type that has been successfully implanted using sutures for many years, such as the Carpentier-Edwards PERIMOUNT Magna® Aortic Heart Valve available from Edwards Lifesciences of Irvine, Calif., though the autonomous nature of the valve member is not absolutely required. In this sense, a "off-the-shelf" prosthetic heart valve is suitable for stand-alone sale and use, typically including a non-expandable, non-collapsible support structure having a sewing ring capable of being implanted using sutures through the sewing ring in an open-heart, surgical procedure.

A primary focus of the present invention is a prosthetic heart valve having a single stage implantation in which a surgeon secures a hybrid valve having an anchoring skirt and valve member to a valve annulus as one unit or piece (e.g., a "unitary" valve). Certain features of the hybrid anchoring skirt and valve member are described in U.S. Pat. No. 8,308,798, filed Dec. 10, 2009, the contents of which are expressly incorporated herein. It should be noted that "two-stage" prosthetic valve delivery disclosed in the aforementioned publication refers to the two primary steps of a) anchoring structure to the annulus, and then b) connecting a valve member, which does not necessarily limit the valve to just two parts. Likewise, the valve described herein is especially beneficial in a single stage implant procedure, but that does not necessarily limit the overall system to just one part. For instance, the heart valve disclosed herein could also use an expanding base stent which is then reinforced by the subsequently implanted heart valve. Because the heart valve has a non-expandable and non-collapsible annular support structure, and a plastically-expandable anchoring skirt, it effectively resists recoil of a self-expanded base stent. That said, various claims appended hereto may exclude more than one part.

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause such as fluid dynamics acting on leaflets or commissures. Conversely, "non-expandable" should not be interpreted to mean completely rigid or a dimensionally stable, as some slight expansion of conventional "non-expandable" heart valves, for example, may be observed.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a mitral valve replacement will be implanted at the mitral annulus. Certain features of the present invention are particularly advantageous for one implantation site or the other, in particular the aortic annulus. However, unless the combination is structurally impossible, or excluded by claim language, any of the heart valve embodiments described herein could be implanted in any body channel.

A "quick-connect" aortic valve bio-prosthesis described herein is a surgically-implanted medical device for the treatment of aortic valve stenosis. The exemplary quick-connect device comprises an implantable bio-prosthesis and a delivery system for its deployment. The device, delivery system and method of use take advantage of the proven hemodynamic performance and durability of existing commercially available, non-expandable prosthetic heart valves, while improving ease of use and reducing total procedure time. This is mainly accomplished by eliminating the need to suture the bio-prosthesis onto the native annulus as is currently done per standard surgical practice, and typically requires 12-24 manually-tied sutures around the valve perimeter. Also, the technique may obviate the need to excise the leaflets of the calcified valve and debride or smooth the valve annulus.

An exemplary hybrid prosthetic heart valve and valve holder is disclosed in U.S. Patent Publication No. 2012/0065729 to Pintor, et al., filed Jun. 23, 2011, to which priority is claimed, and which is hereby expressly incorporated by reference herein.

Figure 5A:
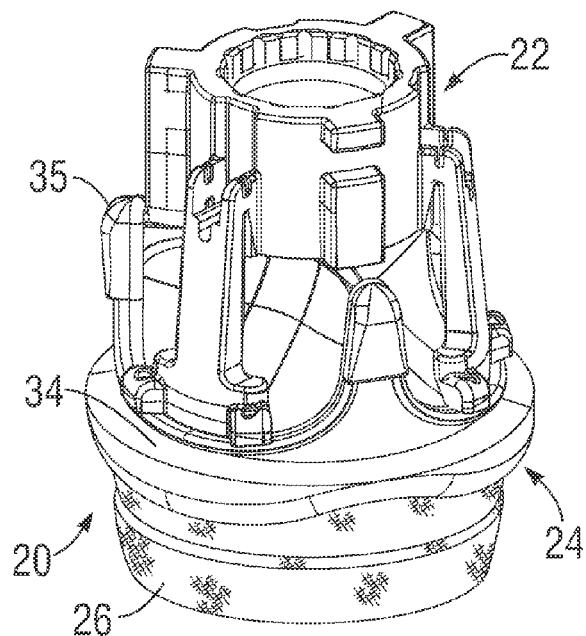
FIGS. 5A and 5B are perspective views of an exemplary prosthetic heart valve of the present application assembled on a valve holder.
Figure 5B:
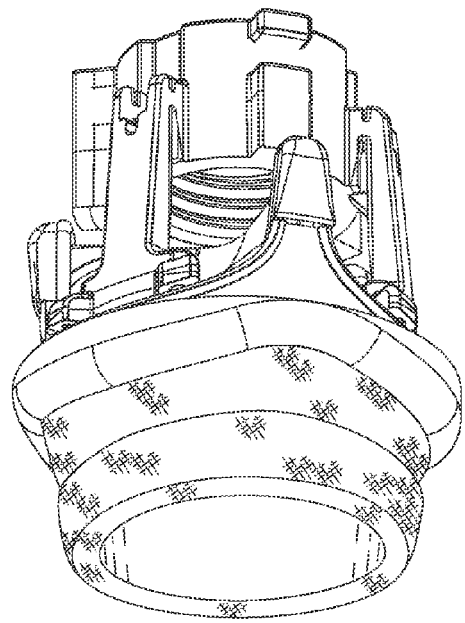
Figure 6A:
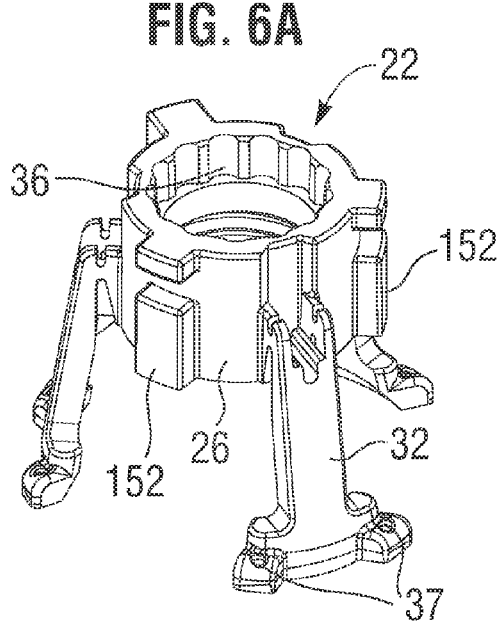
FIGS. 6A and 6B are perspective view of the valve holder of FIGS. 5A and 5B separated from the heart valve.
Figure 6B:
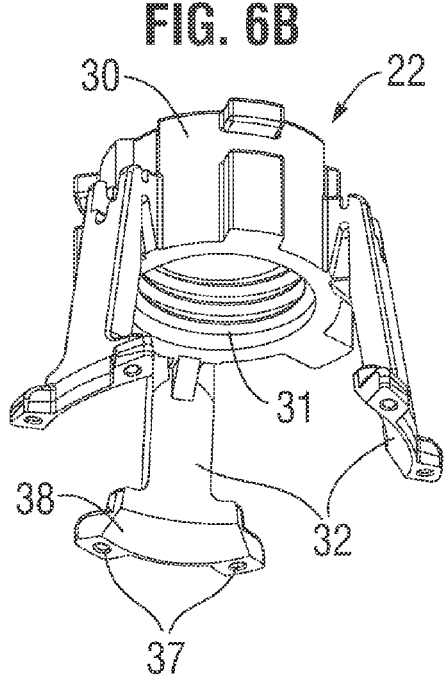

FIGS. 5A and 5B show an exemplary hybrid prosthetic heart valve 20 of the present application assembled on a valve holder 22, while FIGS. 6A and 6B show the valve holder 22 separated from the heart valve 20. As mentioned, the prosthetic heart valve 20 desirably includes a valve member 24 having an anchoring stent or skirt 26 attached to and extending from an inflow end thereof, such as to a sewing ring 28. The valve member 24 is desirably non-collapsible and non-expandable, while the anchoring skirt 26 may expand from the contracted state shown into an expanded state, as will be described.

In one embodiment, the valve member 24 comprises a Carpentier-Edwards PERIMOUNT Magna® Aortic Heart Valve available from Edwards Lifesciences of Irvine, Calif., while the anchoring skirt 26 includes an inner plastically-expandable frame or stent covered with fabric. In another embodiment, the valve member 24 comprises a PERIMOUNT Magna® Aortic valve subjected to GLX tissue treatment, which allows for dry packaging and sterilization and eliminates the need to rinse the valves before implantation.

The general function of the anchoring skirt 26 is to provide the means to attach the prosthetic valve member 24 to the native aortic root. This attachment method is intended as an alternative to the present standard surgical method of suturing aortic valve bio-prostheses to the aortic valve annulus, and is accomplished in much less time. Further, this attachment method improves ease of use by eliminating most if not all suturing. The anchoring skirt 26 may be a pre-crimped, tapered, 316L stainless steel balloon-expandable stent, desirably covered by a polyester fabric to help seal against paravalvular leakage and promote tissue ingrowth once implanted within the annulus.

The completed valve member 24 provides the occluding surfaces for the prosthetic heart valve 20, preferably in the form of flexible bioprosthetic leaflets. For example, the valve leaflets may be taken from another human heart (cadaver), a cow (bovine), a pig (porcine valve) or a horse (equine). Alternatively, the valve member may comprise mechanical components rather than biological tissue. Although an autonomous (i.e., capable of stand-alone surgical implant) flexible leaflet valve member 24 is described and illustrated, alternative valve members that have rigid leaflets, or are not fully autonomous may be substituted.

For bioprosthetic valves, an exemplary process includes storing the prosthetic heart valve 20 in a preservative solution after manufacture and prior to use. A preservative such as glutaraldehyde is provided within a storage jar. This "wet" storage arrangement applies to the illustrated heart valve 20 shown, which includes conventional bioprosthetic leaflets. However, as mentioned above, the heart valve could also be used without a preservative solution for bioprosthetic leaflets that have been dried, such as with the GLX tissue treatment from Edwards Lifesciences, and also for mechanical valves.

The valve holder 22, as seen in the details of FIGS. 6A and 6B, and also in FIGS. 7A-7D and 8A-8C, includes a central tubular hub portion 30 having internal threads 31, and a plurality of stabilizing legs 32 projecting axially and radially outward therefrom. Each of the three stabilizing legs 32 contacts and attaches to a cusp portion 34 of the valve member 24 between commissure posts 35 (see FIGS. 7A and 5A). An upper end of the hub portion 30 also has an internal star-shaped bore 36 that provides a valve-size-specific keyed engagement with a delivery system, as will be explained. The valve holder 22 secures with sutures to the valve member 24 from the time of manufacture to the time of implant, and is stored with the valve member.

Figure 8B:
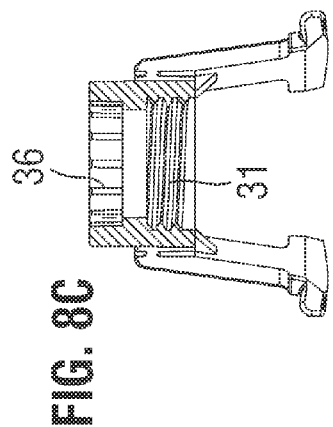
FIGS. 8A-8C are elevational, plan, and sectional views of the exemplary valve holder.
Figure 8A:
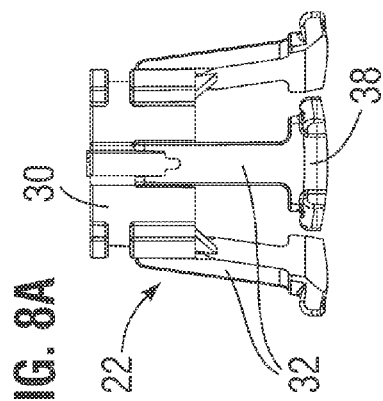
Figure 8C:
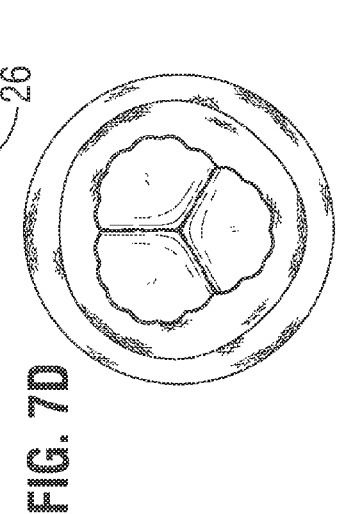
Figure 7C:
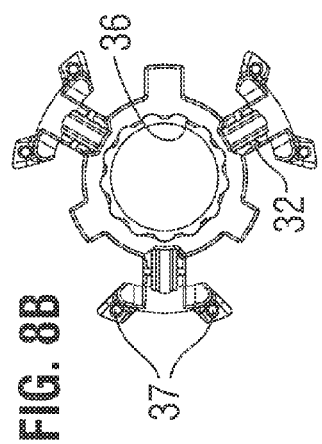
FIGS. 7A-7D are orthogonal views of the exemplary prosthetic heart valve and valve holder.
Figure 7B:
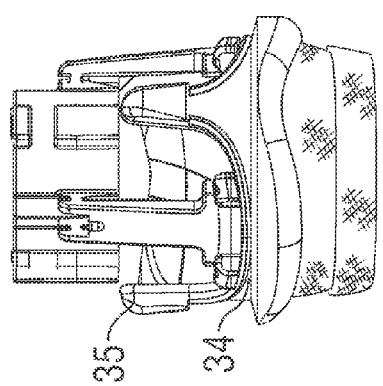
Figure 7A:
Figure 7D:
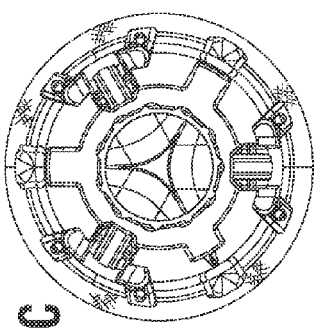

In one embodiment, the holder 22 is formed of a rigid polymer such as Delrin polypropylene that is transparent to increase visibility of an implant procedure. As best seen in FIG. 8B, the holder 22 exhibits openings between the stabilizing legs 32 to provide a surgeon good visibility of the valve leaflets, and the transparency of the legs further facilitates visibility and permits transmission of light therethrough to minimize shadows.

FIGS. 7-8 also illustrate a series of through holes 37 in the legs 32 permitting connecting sutures to be passed through fabric at the cusps 34 of the prosthetic valve member 24 and across a cutting guide in each leg. As is known in the art, severing a middle length of a suture that is connected to the holder 22 and passes through the valve permits the holder to be pulled free from the valve when desired. Each leg 32 extends radially outward and downward from the central hub portion 30 in a substantially constant thickness, terminating at a distal foot 38 which is substantially wider. The distal foot 38 may be twice as wide as the upper portion of the respective leg 32. The through holes 37 pass through circumferentially outer points of each distal foot 38, and are thus spaced significantly apart for each leg 32. This provides six total attachment points between the holder 22 and the valve member 24, all in the cusp regions 34. Moreover, each leg 32 extends down to the center or nadir of each cusp portion 34, which allows the surgeon better access behind and adjacent to the commissure posts. In this regard, the holder 22 is attached to the outflow side of the valve member 24 even though there is some overlap. Furthermore, the spread out nature of the feet 38 and dual attachment points thereon provides an extremely robust holding force between the holder and valve member 24. The configuration of the wide feet 38 and through holes 37 thereon forms an inverted Y-shape of sorts. Prior holders either attached to the top of the commissure posts, or to a single point in the nadir of each cusp. Such holders left the valve prone to twisting or deforming from contact with operating room or anatomical surfaces.

An exemplary implant procedure for the prosthetic heart valve 20 is summarized with reference to in FIGS. 9A-9B and 10A-10B, though a more complete discussion is seen with reference to FIGS. 16A-16J of the Pintor publication. These figures are sectional views through an isolated aortic annulus showing a portion of the adjacent left ventricle and ascending aorta with sinus cavities. The two coronary arteries are also shown. As will be explained, the anchoring skirt 26 is deployed against the native leaflets or, if the leaflets are excised, against the debrided aortic annulus as shown. The anchoring skirt 26 transitions between the tapered constricted shape of FIGS. 9A-9B to its flared expanded shape shown in FIGS. 10A-10B.

In the ensuing procedure drawings, the heart valve 20 is oriented with an inflow end down and an outflow end up. That is, blood flow through the valve 20 is upward as shown in the drawings. Therefore, the terms inflow side and down may be used interchangeably at times, as well as the terms outflow side and up. Furthermore, the terms proximal and distal are defined from the perspective of the surgeon delivering the valve inflow end first, and thus proximal is synonymous with up or the outflow side, and distal with down or the inflow side.

An implant procedure involves delivering the heart valve 20 and expanding the anchoring skirt 26 at the aortic annulus, and potentially tying off or securing one or more sutures. Because the valve member 24 is non-expandable, the entire procedure is typically done using the conventional open-heart technique. However, because the anchoring skirt 26 is implanted by simple expansion, with reduced suturing, the entire operation takes less time. This hybrid approach will also be much more comfortable to surgeons familiar with the open-heart procedures and commercially available heart valves.

A preliminary step in preparing an aortic annulus for receiving the heart valve includes installation of guide sutures 39. The aortic annulus is shown schematically isolated and it should be understood that various anatomical structures are not shown for clarity. The annulus includes a fibrous ring of tissue that projects inward from surrounding heart walls. The annulus defines an orifice between the ascending aorta and the left ventricle. Although not shown, native leaflets project inward at the annulus to form a one-way valve at the orifice. The leaflets may be removed prior to the procedure, or left in place as mentioned above. If the leaflets are removed, some of the calcified annulus may also be removed, such as with a rongeur. The ascending aorta commences at the annulus with three outward bulges or sinuses, two of which are centered at coronary ostia (openings) leading to coronary arteries. As will be seen below, it is important to orient the prosthetic valve member 24 so that its commissure posts 36 are not aligned with and thus not blocking the coronary ostia.

The surgeon attaches the guide sutures 39 at three evenly spaced locations around the aortic annulus. In the illustrated embodiment, the guide sutures 39 attach to locations below or corresponding to the coronary ostia (that is, two guide sutures are aligned with the ostia, and the third centered below the non-coronary sinus). The guide sutures 39 are preferably looped twice through the annulus from the outflow or ascending aorta side to the inflow or ventricular side. Of course, other suturing methods or pledgets may be used depending on surgeon preference.

FIG. 9A shows the heart valve 20 on the distal end of a delivery system 110 and at a desired implant position at the aortic annulus, and during placement of tubular suture snares 120. The sewing ring 28 is positioned supra-annularly, or above the narrowest point of the aortic annulus, so as to allow selection of a larger orifice size than a valve placed intra-annularly, or within the annulus. A dilatation balloon 112 on the distal end of a balloon catheter 114 of the delivery system 110 can be seen just beyond the distal end of the anchoring skirt 26.

The surgeon delivers a plurality of suture snares 120 down each pair of the guide sutures 39 into contact with the upper or outflow side of the sewing ring 28. The snares 120 enable downward pressure to be applied to the ring 28 and thus the valve 20 during the implant procedure, which helps insure good seating of the ring 28 on the annulus. The snares 120 also provide rigid enclosures around each of the flexible guide sutures 39 which helps avoid entanglement with other moving surgical instruments, as will be appreciated. As there are three pairs of guide sutures 39 (six free lengths) three snares 120 are utilized, though more or less is possible. The snares 120 are typically tubular straw-like members of medical grade plastic.

FIG. 9A shows all of the pairs of suture snares 120 bent outward and a majority of the delivery system 110. The delivery system 110 is in a configuration prior to advancement of the balloon catheter 114 and its dilatation balloon 112.

FIG. 9B shows the delivery system after advancement of the balloon catheter 114 and dilatation balloon 112 relative to a handpiece 204 on a proximal end of an elongated handle shaft 130. Although it will be described in greater detail below with respect to FIGS. 11-12, the handle shaft 130 terminates in a valve holder adapter 208 that directly connects to the holder 22. The handle shaft 130 is desirably malleable for manipulating the orientation of the heart valve 20 during delivery through the ascending aorta.

After distal advancement, the balloon 112 projects downward through the valve 20, and into the left ventricle. As will be explained below, the delivery system 110 provides binary position displacement of the balloon 112, either retracted substantially within the prosthetic heart valve 20 or advanced precisely as far as necessary to expand the anchoring skirt 26 of the valve.

FIG. 10A shows the dilatation balloon 112 inflated to expand the anchoring skirt 26 against the ventricular side of the aortic annulus. The balloon 112 desirably has a frustoconical profile that expands the anchoring skirt 26 into a frustoconical expanded state. Not only does this conform better to the subannular contours but over expands somewhat the annulus such that a larger valve maybe utilized than without the expansion. One advantage of using a plastically-expandable stent is the ability to expand the native annulus to receive a larger valve size than would otherwise be possible with conventional surgery. Desirably, the left ventricular outflow tract (LVOT) is significantly expanded by at least 10%, or for example by 1-5 mm, and the surgeon can select a heart valve 20 with a larger orifice diameter relative to an unexpanded annulus. Even a 1 mm increase in annulus size is significant since the gradient is considered to be proportional to the radius raised to the $4^{th}$ power.

Simple interference between the anchoring skirt 26 and the annulus may be sufficient to anchor the heart valve 20, or interacting features such as projections, hooks, barbs, fabric, etc. may be utilized. For example, a distal end of the anchoring skirt may expand more than the rest of the anchoring skirt so that peaks in the strut row farthest from the prosthetic valve project outward into the surrounding annulus. Also, the balloon 112 may have a larger distal expanded end than its proximal expanded end so as to apply more force to the free end of the anchoring skirt 26 than to the prosthetic valve member 24. In this way, the prosthetic valve member 24 and flexible leaflets therein are not subject to high expansion forces from the balloon 112.

The balloon 112 desirably is tapered to have an angle between about 0-45°, and more preferably is about 38° (0° being a cylindrical expansion). Alternatively, the balloon 112 may include curves or non-axi-symmetric contours to deform the anchoring skirt 26 to various desired shapes to fit better within the particular annulus. Indeed, various potential shapes are described in U.S. Patent Publication 2008/0021546, entitled System for Deploying Balloon-Expandable Heart Valves, published Jan. 24, 2008, the disclosure of which is expressly incorporated herein.

FIG. 10B then illustrates the balloon 112 deflated and contracted. A spring mechanism within the delivery system 110 along with longitudinal pleats in the balloon 112 facilitate contraction of the balloon when deflated into an extremely narrow configuration which makes removal easier.

The next step is retraction of the balloon 112 and entire delivery system 110 from the valve holder 22 before or after removal of the snares 120, which happens only as a contingency. Although not shown, the most common procedure after expansion of the balloon 112 and skirt 26 involves the surgeon severing the connecting sutures between the valve holder 22 and the prosthetic valve member 24, and removing the entire delivery system. Severing a middle length of each suture that connects the holder 22 to the valve member 24 permits the delivery system 110 with the holder at the distal end to be pulled free from the valve 20. However, the delivery system 110 also features a simple engagement and detachment mechanism that enables the surgeon to easily remove the system 110 from the holder 22 which remains attached to the valve 20. This detachment may be needed to replace the balloon catheter, such as if the original balloon develops a leak or for some reason does not deploy properly. This "quick-release" arrangement permits the surgeon to rapidly exchange catheters while leaving the valve 20 in place.

Finally, the prosthetic heart valve 20 is fully implanted with the guide sutures 39 knotted on the proximal face of a sewing ring 28. The guide sutures 39 are primarily for rotationally orienting the heart valve 20 as it seats against the aortic annulus and to define a plane for axial positioning. As such, the guide sutures 39 are not believed strictly necessary for securing the heart valve 20 at the annulus. Moreover, devices other than knots such as clips or cinches could be used to secure the guide sutures 39 speed up the process.

FIGS. 11A-11C are perspective views illustrating deployment of the balloon catheter through the prosthetic heart valve and expansion of the balloon to expand the anchoring skirt, analogous to FIGS. 9-10.

FIG. 11C shows the balloon 112 inflated to expand and deploy the anchoring skirt 26 against the annulus. The anchoring skirt 26 transitions between its conical contracted state and its generally tubular or slightly conical expanded state. Simple interference between the anchoring skirt 26 and the annulus may be sufficient to anchor the heart valve 20, or interacting features such as projections, hooks, barbs, fabric, etc. may be utilized. For example, a distal end of the anchoring skirt (see lower edge 94 in FIG. 19B) may be expanded more than the rest of the anchoring skirt so that peaks in the strut row farthest from the prosthetic valve project outward into the surrounding annulus.

Also, the balloon 112 may have a larger distal expanded end than its proximal expanded end so as to apply more force to the free end of the anchoring skirt 26 than to the prosthetic valve member 24. In this way, the prosthetic valve member 24 and flexible leaflets therein are not subject to high expansion forces from the balloon 112.

FIGS. 12A-12C illustrate a preferred configuration for coupling the delivery system 110 to the prosthetic heart valve 20 and holder 22 assembly. In particular, a tubular balloon introducer sleeve 212 threads within the holder 22. Preferably, the user couples the introducer sleeve 212 to the holder 22 at the time of preparing the valve 20 for surgery, and more preferably the sleeve 212 may be used to extract the valve 20 from its storage jar. A portion of the sleeve 212 projects in a proximal direction from within the holder 22 and presents a tubular entryway for the balloon wire tip 210 and balloon 112. The user inserts the delivery system 110 through the introducer sleeve 212 until the valve holder adapter 208 contacts the holder 22.

With reference to FIG. 12A, the valve holder adapter 208 includes an elongated through bore which receives the proximal end of the introducer sleeve 212. Although not shown, a plurality of cantilevered fingers extend longitudinally along the adapter 208 terminating at its distal end. Each of the fingers includes an inwardly directed bump 218 (FIG. 12A). Sliding the adapter 208 over the introducer sleeve 212 such that the distal end contacts a proximal end of the holder 22 brings the bumps 218 over an external groove (not numbered) on the exterior of the sleeve 212 so as to provide an interference connection. A locking sleeve 206 then slides over the holder adapter 208, as seen in FIG. 12A. Because the inner bore of the locking sleeve 206 fits closely around the adapter 208, the cantilevered fingers are retained in their aligned orientation with the bumps 218 in the groove of the sleeve 212. The locking sleeve 206 desirably frictionally engages the exterior of the adapter 208 to prevent two parts from easily coming apart. Alternatively, a separate detente or latch may be provided for more security. Ultimately, when the locking sleeve 206 is in the position of FIG. 12A, the delivery system 110 is securely coupled to the valve holder 22. Moreover, the balloon 112 extends through the balloon introducer sleeve 212 to be positioned within the expandable skirt 26.

Another advantageous feature of the present application is a keyed engagement between delivery systems 110 and holders 22 for the same size of heart valves. In particular, the hub portion 30 of the holder 22 has an internal star-shaped bore 38 (see FIG. 8B) which is sized and patterned to be keyed to an external star-shaped rim provided on the holder adapter 208 (not numbered). Because the balloon catheter 114 is integrated with the delivery system 110, and each balloon catheter is sized for a particular valve, only the delivery system 110 which is designed for that particular valve should be coupled to its holder. That is, each expansion skirt 26 must be expanded to a particular diameter, which requires different sizes of balloons 112. Consequently, each differently sized valve holder and a delivery system combination has a unique star-shaped pattern which prevents mating with a different size.

Typically, the delivery system 110 is packaged separately from the heart valve 20 and holder 22, and this keying arrangement prevents misuse of the wrong delivery system. Additionally, if the balloon breaks and another delivery system must be rapidly obtained and utilized, the keying arrangement prevents the wrong delivery system from being substituted. There are typically 6-8 valve sizes in 2 millimeter increments, and thus a similar number of unique keyed couplings will be provided. Furthermore, the star-shaped pattern disclosed permits engagement at a plurality of rotational orientations. In a preferred embodiment, the user must rotate the delivery system 110 no more than 30° before the star-shaped rim of the adapter 208 mates with the internal star-shaped bore 36 of the holder 22. This is extremely beneficial if changing out the delivery system 110, because the original elongated handle shaft 130 may be bent into a particular orientation which is much easier to replicate if the keyed features do not have to be oriented in only one or two angular relations.

As mentioned, the elongated handle shaft 130 is malleable or bendable into various shapes. This bendability of the handle shaft 130 significantly enhances the ability of a surgeon to correctly position the heart valve 20 as it advances toward the annulus. Often, access passageways into the heart during a surgical procedure are somewhat confined, and may not provide a linear approach to the annulus. Accordingly, the surgeon bends the handle shaft 130 to suit the particular surgery. Various materials and constructions may be utilized to provide a malleable tube for use as the handle shaft 130. The handle shaft 130 must be axially rigid so that the user can position the heart valve in the annulus with confidence. In a preferred embodiment, an aluminum tube having a chromate (e.g., Iridite) coating is used. Aluminum is particularly well-suited for forming small tubes that can be bent without kinking, but should be coated with Iridite or the like to prevent deterioration in and reaction with the body.

A balloon inflation tube 199 and balloon extension wire 200 are formed of materials that have column strength but are relatively flexible in bending. The wire may be Nitinol while the inflation tube 199 is desirably formed of a braid reinforced thermoplastic elastomer (TPE) such as a polyether block amide known under the trade name of PEBAX® (Arkema of Colombes, France).

As the delivery system 110 may be subjected to several bends in use, care must be taken to ensure that the concentric tubes and wire do not introduce misalignment. That is, smaller diameter objects tend to travel shorter paths within larger concentric tubes, thus cause them to extend out of the distal end of the tubes after being bent. As such, the balloon inflation tube 199 is desirably closely sized to match the inner diameter of the malleable handle shaft 130. This close matching of tube sizes ensures that the axial position of the balloon 112, which is affixed to the end of the balloon inflation tube 199, does not shift much relative to the axial position of the prosthetic heart valve 20, which is affixed relative to the end of the malleable handle shaft 130. The balloon extension wire 200 has a size relative to the ID of the balloon inflation tube 199 sufficient to permit good flow of saline when filling the balloon 112.

Figure 3:
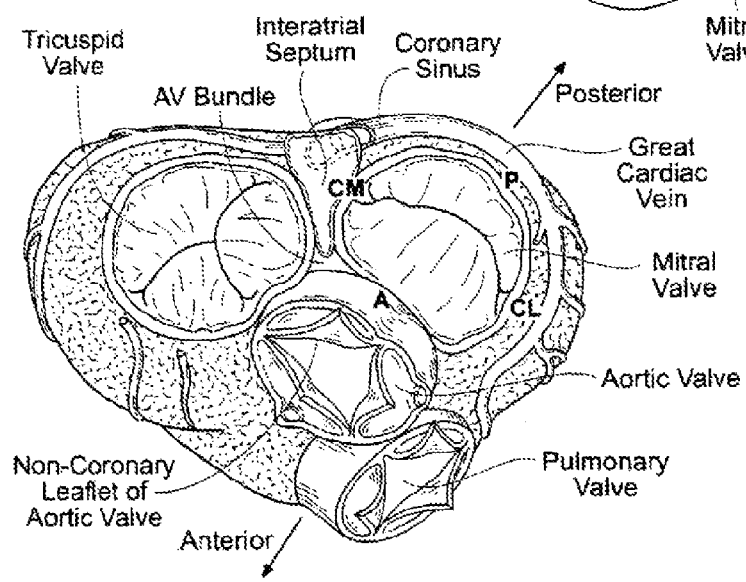
FIG. 3 is an anatomic superior view of a section of the human heart shown in FIG. 2, with the tricuspid and mitral valves closed and the aortic and pulmonary valves opened during ventricular systole (ventricular emptying) of the cardiac cycle.

The present application also provides an improved balloon 112 and system for deploying and removing it, as seen best in FIGS. 12A-12C. As seen in the deflated views, the balloon 112 preferably comprises a plurality of longitudinal pleats which help reduce its radial configuration for passage through the delivery system 110. Furthermore, the balloon extension wire 200 extends through the balloon inflation tube 199, through the dilatation balloon 112, and terminates in a molded balloon wire tip 210 affixed to the distal end of the balloon. The path of the wire 200 is seen in the sectional views of FIGS. 3A and 4A. Although the proximal end of the balloon 112 fastens to the inflation tube 199, and thus from there to the handpiece 204, the distal tip 210 does not. Instead, the wire 200 fastens to a spring compression pin 196 which translates within a lumen in a proximal end cap 190, and engages the balloon extension spring 194 therein. In this regard, the balloon extension wire 200 moves independently within the delivery system 110 instead of being fixedly attached. This, in turn, allows the distal end of the balloon 112 to move with respect to the proximal end.

The exemplary delivery system balloon 112 has a relatively high diameter-to-length ratio compared to other surgical balloons, such as those used to expand cardiovascular stents. This makes it particularly difficult for the balloon 112 to return to a small geometry upon deflation after deployment. Balloons of such size ratios tend to "butterfly" by forming wings that prevent removal through the valve holder without the application of high forces, which may cause damage to the valve itself. The exemplary delivery system 110 and balloon 112 include several advances from earlier heart valve delivery systems that facilitate atraumatic removal of the balloon 112. First, as mentioned above, a series of longitudinal pleats are heat set into the wall of the balloon 112 to facilitate self-collapse during deflation. Further, the distal end of the balloon 112 moves relative to the proximal end to enable lengthening of the balloon during deflation. This lengthening occurs automatically by virtue of the wire 200 which is spring-biased to stretch the balloon longitudinally. It should be noted that easy deflation and removal of the balloon 112 permits rapid replacement of the balloon catheter in case of a problem, such as insufficient inflation.

Figure 4:
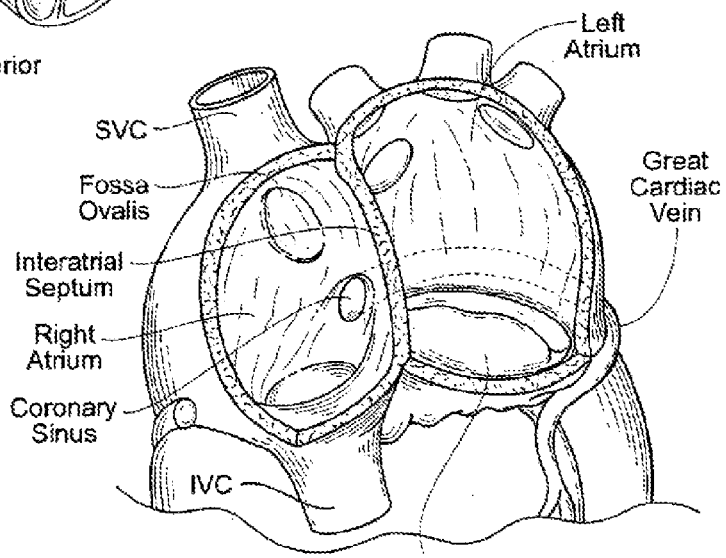
FIG. 4 is an anatomic anterior perspective view of the left and right atria, with portions broken away and in section to show the interior of the heart chambers and associated structures, such as the fossa ovalis, coronary sinus, and the great cardiac vein.

FIG. 12A is a sectional view with the balloon 112 advanced as in FIG. 4A. In this configuration, the spring 194 has a length of $x_1$, and the spring compression pin 196 is all the way to the right within the end cap cavity. In this "resting" state with the balloon 112 deflated, the spring 194 may be relaxed or under a slight compressive preload. Subsequently, saline is introduced via the proximal luer connector 192 and travels distally along the length of the balloon catheter components to inflate the balloon 112. Inflation of the balloon 112 causes radial expansion but axial foreshortening, thus displacing the distal tip 210 to the left as shown in FIG. 12B. This, in turn, displaces the balloon extension wire 200 and attached spring compression pin 196 to the left against the resiliency of the spring 194. Ultimately, the spring is compressed to a second shorter length $x_2$. In a preferred embodiment, the spring 194 undergoes complete compression to its solid length so as to provide a positive stop on proximal movement of the wire 200 and attached balloon distal tip 210. This helps ensure proper expansion of the anchoring skirt 26, as will be more fully explained. The proximal movement of the distal tip 210 against the reaction force of the spring 194 places the wire 200 in compression.

Finally, FIG. 12C illustrates deflation of the balloon 112 by pulling a vacuum through the inflation movement and return movement to the right of the distal tip 210 and balloon extension wire 200. This movement is encouraged, and indeed forced, by expansion of the spring 194. The force of the spring 194 is calibrated so as to elongate the pleated balloon 112 so it assumes its previous radially constricted diameter, or as close as possible to it. Furthermore, the wire 200 may be rotated about its axis to further encourage constriction of the balloon 112 by causing the pleats to further fold in a helical fashion. This can be accomplished by extending a portion of the wire 200 from the proximal end of the Luer connector 192 so as to be grasped and rotated by forceps, or otherwise providing a lever or thumb plunger (not shown) fastened to the wire and projecting laterally from the system. Still further, the spring compression pin 196 may be constrained to translate within a helical track. In the latter case, the pin 196 may include a bayonet-type mount that locks within detents in both ends of the helical track. The spring-biased lengthening and consequent radial contraction of the balloon 112 facilitates its proximal removal through the now-deployed prosthetic heart valve 20.

As mentioned above, the balloon 112 desirably has a frustoconical profile that expands the anchoring skirt 26 into a frusto-conical expanded state. More typically, and as shown in FIG. 12B, the balloon 112 is generally spherical when expanded. Nevertheless, a spherical balloon will outwardly expand the anchoring skirt 26 into a frusto-conical shape due to the connection at one end of the inner stent frame 80 to the heart valve sewing ring 28. To ensure sufficient and proper outward expansion of the anchoring skirt 26, the balloon 112 is axially positioned such that a midline 280 indicated around the maximum circumference (equatorial line) thereof registers with the distalmost end 282 of the skirt. In doing so, the widest part of the balloon 112 corresponds to the end of the skirt 26, which tends to expand the skirt conically. A tolerance of 1-2 mm between the location of the midline 280 and the distalmost end 282 of the skirt is acceptable which may occur for different sizes of valves and associated skirt 26.

FIG. 12A shows an exemplary stepped balloon construction wherein the balloon 112 is desirably offset molded to form the midline 280 as a small step in the balloon wall. That is, the opposed balloon mold halves will have a slightly different diameter, such that a physical step in the final product is formed—the midline 280. Alternatively, the midline 280 may be formed by a small equatorial rib or indent formed in the mold process, or even with an ink marking, though the latter may not be suitable for surgical application. The midline 280 will be visible on the balloon 112 in both its deflated and inflated states, and is extremely useful as a reference line during assembly and quality control of the delivery system 110. For instance, the components of the system 110 are assembled and the location of the balloon 112 in its advanced position is checked against the anchoring skirt 26. Since the balloon 112 foreshortens when it is inflated, the reference midline 280 should be beyond the distalmost end 282 of the skirt 26 when the balloon is deflated, a location that can easily be inspected during assembly.

It should be noted that the flared shape of the expanded anchoring stent 26 (see FIG. 21B, below) may help improve flow through the prosthetic heart valve relative to a valve without the skirt. In some patients, ventricular hypertrophy tends to cause an inward bulging of the left ventricle wall just below the aortic valve. The conical skirt 26 will expand outward against this anomaly, and in doing so will expand the inflow passage to the aortic valve.

It should be mentioned that as an alternative to a balloon, a mechanical expander may be used to expand the anchoring skirt 26 shown above. For instance, a mechanical expander may include a plurality of spreadable fingers actuated by a syringe-like apparatus, as seen in U.S. Pat. No. 8,308,798, filed Dec. 10, 2009, incorporated herein. The fingers are axially fixed but capable of pivoting or flexing with respect to a barrel. The distal end of a plunger has an outer diameter that is greater than the diameter circumscribed by the inner surfaces of the spreadable fingers, such that distal movement of the plunger with respect to the barrel gradually cams the fingers outward within the coupling stent. Alternatives include mechanical fingers that are not pivotally attached to a handle attachment member. In this way, an inflation balloon causes direct radial expansion of the fingers instead of a pivoting movement. Therefore, the term "expansion catheter" pertains to balloon catheters, purely mechanical spreaders on the end of a catheter, or combinations thereof. Also, "plastically-expandable" encompasses materials that can be substantially deformed by an applied force, such as by a balloon or a mechanical spreader, to assume a different shape. Some self-expanding stents may be deformed to a degree by an applied force beyond their maximum expanded dimension, but the primary cause of the shape change is elastic rebound as opposed to a plastic deformation.

FIGS. 13-19 illustrate a number of steps in the construction of the prosthetic heart valve 20.

FIG. 13 illustrates an inner structural band subassembly 40 including an inner polymer band 42 having three upstanding posts 44 and a scalloped lower ring 46, and an outer more rigid band 48 having a scalloped shape to conform to the lower ring 46. The band subassembly 40 is formed by positioning the polymer band 42 within the rigid band 48 and securing them together with sutures through aligned holes, for example.

FIG. 14 is a perspective view of a further subassembly of an undulating cloth-covered wireform 50. FIG. 14A is a detailed sectional view of a cusp portion of the wireform 50 showing an inner wire member 52 covered with fabric that defines a tubular portion 54 and an outwardly projecting flap 56. The wireform 50 defines three upstanding commissure posts 58 and three downwardly convex cusps 60. This is a standard shape for tri-leaflet heart valves and mimics the peripheral edges of the three native aortic leaflets. The shape of the wireform 50 coincides with the upper edge of the band subassembly 40, and defines the outflow edge of the prosthetic valve 20. The band subassembly 40 and wireform 50 are then joined together with a cloth interface and outer sewing ring, and then with flexible leaflets as will be shown.

FIG. 15 is a perspective view of the assembled band subassembly 40 and sewing ring 62, while FIG. 15A shows details through a cusp portion thereof. The two structural bands 42, 48 are the same heights in the cusp region and encompassed by a fabric cover 64 that is rolled into a peripheral tab 66. The sewing ring 62 comprises an inner suture permeable member 68 having a frustoconical form and encompassed by a second fabric cover 70. The two fabric covers 64, 70 are sewn together at a lower junction point 72.

FIGS. 16A and 16B are inflow and outflow perspective views, respectively, of the surgical heart valve member 24 before coupling with an inflow anchoring skirt to form the prosthetic heart valve 20. Although construction details are not shown, three flexible leaflets 74 are secured along the undulating wireform 50 and then to the combination of the band subassembly 40 and sewing ring 62 shown in FIG. 15. The entire structure at the commissures is covered with a secondary fabric to form the valve commissures 35 as seen in FIG. 19A.

In a preferred embodiment, and as seen in the cutaway portion of FIG. 20, each of the three leaflets 74 includes outwardly projecting tabs 75 that pass through the inverted U-shaped commissure posts 58 and wrap around the cloth-covered upstanding posts 44 of the inner polymer band 42 (see FIG. 15). Tabs 75 from adjacent leaflets converge outside of the wireform commissure posts 58 and are sewn together to provide an outer anchor for the leaflet free edges 76. In use, fluid forces close the leaflets (coaptation) as seen in FIG. 20 and exert substantial force on the occluded valve, which translates into inward force on the leaflet free edges. The assembly of the wrapped leaflet tabs 75 and cloth-covered posts 44 sewn together provides a solid anchor that is prevented from inward movement by the metallic wireform posts 58. Some flexing is acceptable.

As stated previously, the completed valve member 24 shown in FIGS. 16A and 16B provides the occluding surfaces for the prosthetic heart valve 20 described herein. Although an autonomous (i.e., capable of stand-alone surgical implant) flexible leaflet valve member 24 is described and illustrated, alternative valve members that have rigid leaflets, or are not fully autonomous may be substituted. In various preferred embodiments, the valve leaflets may be taken from another human heart (cadaver), a cow (bovine), a pig (porcine valve) or a horse (equine). In other preferred variations, the valve member may comprise mechanical components rather than biological tissue.

One feature of the valve member 24 that is considered particularly important is the sewing ring 62 that surrounds the inflow end thereof. As will be seen, the sewing ring 62 is used to attach the anchoring skirt 26 to the valve member 24. Moreover, the sewing ring 62 presents an outward flange that contacts and outflow side of the part of annulus, while the anchoring skirt 26 expands and contracts the opposite, ventricular side of the annulus, therefore securing the heart valve 20 to the annulus from both sides. Furthermore, the presence of the sewing ring 62 provides an opportunity for the surgeon to use conventional sutures to secure the heart valve 20 to the annulus as a contingency.

The preferred sewing ring 62 defines a relatively planar upper or outflow face and an undulating lower face. Cusps of the valve structure abut the sewing ring upper face opposite locations where the lower face defines peaks. Conversely, the valve commissure posts align with locations where the sewing ring lower face defines troughs. The undulating shape of the lower face advantageously matches the anatomical contours of the aortic side of the annulus AA, that is, the supra-annular shelf. The ring 62 preferably comprises a suture-permeable material such as rolled synthetic fabric or a silicone inner core covered by a synthetic fabric. In the latter case, the silicone may be molded to define the contour of the lower face and the fabric cover conforms thereover.

Now with reference to FIGS. 17 and 18, assembly of the cloth-covered anchoring skirt 26 will be described. It should first be noted that the size of the anchoring skirt 26 will vary depending on the overall size of the heart valve 20. Therefore the following discussion applies to all sizes of valve components, with the dimensions scaled accordingly.

The general function of the anchoring skirt 26 is to provide the means to attach the prosthetic valve member 24 to the native aortic root. This attachment method is intended as an alternative to the present standard surgical method of suturing aortic valve bio-prostheses to the aortic valve annulus, and is accomplished in much less time. Further, this attachment method improves ease of use by eliminating most of not all suturing. The anchoring skirt 26 may be a pre-crimped, tapered, 316L stainless steel balloon-expandable stent, desirably covered by a polyester fabric to help seal against paravalvular leakage and promote tissue ingrowth once implanted within the annulus. The anchoring skirt 26 transitions between the tapered constricted shape of FIGS. 12A-12B to its flared expanded shape shown in FIG. 16J below.

The anchoring skirt 26 comprises an inner stent frame 80, a fabric covering 82, and a band-like lower sealing flange 84. The inner stent frame 80 will be described in greater detail below, but preferably comprises a tubular plastically-expandable member having an undulating or scalloped upper end 86. The stent frame 80 assembles within a tubular section of fabric 82 which is then drawn taut around the stent frame, inside and out, and sewn thereto to form the intermediate cloth-covered frame 88 in FIG. 17. It should be noted that FIG. 17 shows the stent frame 80 in a tubular, uncrimped state. During this assembly process, the stent frame 80 may remain tubular, and later the frame will be crimped to a conical shape as see in FIG. 19B for example. Of course, the frame 80 may be crimped first and then covered with cloth.

A particular sequence for attaching the tubular section of fabric 82 around the stent frame 80 includes providing longitudinal suture markers (not shown) at 120° locations around the fabric to enable registration with similarly circumferentially-spaced, commissure features on the stent frame. After surrounding the stent frame 80 with the fabric 82, a series of longitudinal sutures at each of the three 120° locations secure the two components together. Furthermore, a series of stitches are provided along the undulating upper end 86 of the stent frame 80 to complete the fabric enclosure. In one embodiment, the tubular section of fabric 82 comprises PTFE cloth, although other biocompatible fabrics may be used.

Subsequently, the lower sealing flange 84 shown in FIG. 18 is attached circumferentially around a lower edge of the intermediate cloth-covered frame 88. First, a linear band 90 of a single layer of fabric, preferably knitted, is formed into a ring and its ends sutured together using a butt joint (not shown). The ring is placed around the intermediate cloth-covered frame 88, aligned with a lower edge thereof, and sewn thereto. Preferably, a series of stitches are formed at and adjacent to the commissure markers previously described. Alternatively, two circumferential lines of stitches may be provided around the lower sealing flange 84 to provide greater anchoring.

The material of the lower sealing flange 84 may vary, but preferably provides a compressible flange about the lower edge of the anchoring skirt 26. For example, the lower sealing flange 84 may be a knitted PTFE fabric in a single layer or multiple layers, Teflon, a silicone ring covered by fabric, or other similar expedients. Furthermore, the sealing flange 84 may not comprise fabric at all, but may be a hydrophilic coating, fibrin glue, or other such substance that helps prevent leakage around the outside of the anchoring skirt 26. The main functions of the fabric layers covering the frame 88 are to help prevent paravalvular leaks and provide means to securely encapsulate any Calcium nodules on the aortic valve leaflets (if left in place) and/or the aortic valve annulus. Covering the entire anchoring skirt 26 eliminates exposed metal and decreases the risk of thromboembolic events and abrasion. In a preferred embodiment, the sealing flange 84 has an axial dimension of between about 2-5 mm, and is spaced from the upper end 86 of the frame 80 by a distance that varies between 2-5 mm. The lower end of the frame may also be scalloped to follow the upper end 86, in which case the sealing flange 84 may also undulate to maintain an even distance with the upper end 86. If a knitted PTFE fabric, the sealing flange 84 desirably has a radial thickness of at least twice the thickness of the tubular fabric 82.

FIG. 19A shows the surgical heart valve member 24 above the cloth-covered anchoring skirt 26 and one way to couple the two elements using sutures. FIG. 19B illustrates the inner stent frame 80 with cloth covering removed to indicate a preferred pattern of coupling sutures passed therethrough. FIG. 20 illustrates an assembled prosthetic heart valve 20 with the valve member 24 attached to the cloth covered anchoring skirt 26 (it should be noted that the anchoring skirt 26 is shown in its expanded configuration which occurs only after implantation).

The anchoring skirt 26 preferably attaches to the sewing ring 62 during the manufacturing process in a way that preserves the integrity of the ring and prevents reduction of the valve's effective orifice area (EOA). Desirably, the anchoring skirt 26 will be continuously sutured to the ring 62 in a manner that maintains the contours of the ring. In this regard, sutures may be passed through apertures or eyelets 92 arrayed along the upper or first end 86 of the inner stent frame 80. Other connection solutions include prongs or hooks extending inward from the stent, ties, Velcro, snaps, adhesives, etc. Alternatively, the anchoring skirt 26 may be more rigidly connected to rigid components within the prosthetic valve member 24.

The inner stent frame 80 seen in FIG. 19B, and in greater detail in FIGS. 21A and 21B may be similar to an expandable stainless steel stent used in the Edwards SAPIEN Transcatheter Heart Valve. However, the material is not limited to stainless steel, and other materials such as Co—Cr alloys, etc. may be used. In one embodiment, the radial thickness of the plurality of struts is around 0.4-0.6 mm. In a preferred embodiment, the material used should have an elongation at break greater than 33%, and an ultimate tensile strength of greater than about 490 MPa. The stent frame 80 may be initially formed in several ways. For instance, a tubular portion of suitable metal such as stainless steel may be laser cut to length and to form the latticework of chevron-shaped interconnected struts. After laser cutting, the stent frame 80 is desirably electro-polished. Other methods including wire bending and the like are also possible. Ultimately, the inner stent frame 80 assumes a crimped, tapered configuration that facilitates insertion through the calcified native aortic valve (see FIG. 7A).

It should be noted that the stent frame 80 as seen in FIG. 19B is slightly different than that shown in FIG. 21A. Namely, the former is shown with a wholly conical constricted configuration. In contrast, the stent frame 80 in FIG. 21A commences at its upper end in a generally tubular shape and then angles inwardly to be tapered toward its lower end. That is, the generally tubular portion has a height h which is only a portion of the total height H. As shown, the tubular portion has a height h which generally corresponds to the height between the troughs 93*a* and the peaks 93*b* of the upper end of the stent. Desirably, the height h of the peaks 93*b* above the troughs 93*a* is between about 25-36% of the total stent height H, with the ratio gradually increasing for larger valve sizes. Because of the two different profiles, the diameter d of the lower end of the stent is somewhat larger than it would be if the stent was crimped to be completely conical. This reduces the amount of bending required by the balloon upon expansion, and thus reduces the stress between the stent and valve member at the time of expansion. Furthermore, because the portion of the stent 80 that is above the troughs 93*a* remains generally tubular even after expansion by the balloon, the area of the stent immediately below the aortic valve annulus commissures (and below the sewing ring 62 upward rises) seats better on the shelf-like annulus.

Figure 22A:
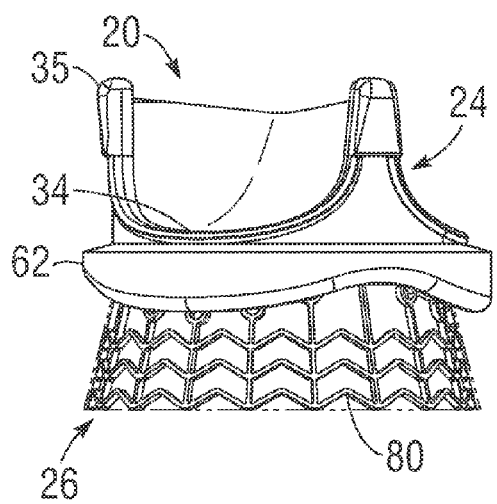
FIGS. 22A and 22B are views of exemplary prosthetic heart valve disclosed herein, shown respectively assembled and with an expandable skirt exploded from a valve component.

With reference to both FIG. 19B and FIG. 21A, the constricted stent frame 80 of the anchoring skirt 26 has a tapered configuration with a lower edge 94 describing a circle having a smaller diameter than a circle described by the upper end 86. The upper end 86 follows an undulating path with alternating arcuate troughs 93*a* and pointed peaks 93*b* that generally corresponds to the undulating contour of the underside of the sewing ring 62 (see FIG. 7B). As mentioned, the anchoring skirt 26 attaches to an inflow end of the valve member 24, typically via sutures through the upper end 86 of the stent frame 80 connected to fabric on the valve member 24 or sewing ring 62. The particular sewing ring 62 as shown in FIGS. 20 and 22A includes an undulating inflow contour that dips down, or in the inflow direction, in the regions of the valve cusps 34, and arcs up, in the outflow direction, in the regions of the valve commissures 35. This undulating shape generally follows the inflow end of the heart valve member wireform 50 (see FIG. 14) which seats down within the sewing ring 62. The scalloped upper end 86 of the stent frame 80 also conforms to this undulating shape, with peaks 93*b* aligned with the valve commissures 35 and valleys 93*a* aligned with the valve cusps 34. Further details on exemplary valve/stent constructions are provided below with reference to FIGS. 42-45.

The mid-section of the frame 80 has three rows of expandable struts 98 in a sawtooth pattern between axially-extending struts 100. The axially-extending struts 100 are in-phase with the peaks 93*b* and troughs 93*a* of the upper end 86 of the stent. The reinforcing ring defined by the thicker wire upper end 86 is continuous around its periphery and has a substantially constant thickness or wire diameter interrupted by the aforementioned eyelets 92. Note that the attachment sutures ensure that the peaks of the upper end 86 of the skirt 26 fit closely to the troughs of the sewing ring 62, which are located under the commissures of the valve.

The minimum ID of the upper end 86 of the covered skirt 26 will always be bigger than the ID of the prosthetic valve member 24 to which it attaches. For instance, if the upper end 86 secures to the underside of the sewing ring 62, which surrounds the support structure of the valve, it will by definition be equal to or larger than the ID of the support structure (which defines the valve orifice and corresponding labeled valve size).

FIG. 21B illustrates the stent frame 80 isolated and in its expanded configuration. The lower end 94 has a diameter D which is larger than the diameter of the upper end 86. The expanded shape of the stent 80 is also preferably slightly flared outward toward its lower end, as shown, by virtue of expanding with a spherical balloon. This shape helps the stent conform to the contours of the left ventricle, below the aortic valve, and thus helps anchor the valve in place.

The specific dimensions of the stent frame 80 for different sizes of valves are presented below in Tables I and II. Although these sizes are exemplary only, they provide trends in terms of what is believed to be desirable for ensuring that the various valve sizes are securely held at the aortic annulus and prevent paravalvular leakage.

TABLE I

Anchoring stent 80 dimensions, pre-crimped tube

| Valve Size (mm) | Total Height (mm) | Height from lower end to valleys 93a (mm) | Tube OD (mm) | Tube Wall Thickness (mm) |
|---|---|---|---|---|
| 19 | 8.4 | 6.0 | 19 | 0.5 |
| 21 | 9.4 | 6.6 | 19 | 0.5 |
| 23 | 10.4 | 7.2 | 23 | 0.55 |
| 25 | 11.6 | 8.00 | 25 | 0.55 |
| 27 | 11.9 | 8.00 | 27 | 0.6 |
| 29 | 12.3 | 8.00 | 29 | 0.6 |

TABLE II

Anchoring stent 80 dimensions, crimped

| Valve Size (mm) | Height from lower end to valleys 93a (mm) | Peak Height, h (mm) | Bottom diameter constricted, d (mm) |
|---|---|---|---|
| 19 | 5.4 | 7.9 | 14.5 |
| 21 | 5.9 | 8.7 | 15.8 |
| 23 | 6.4 | 9.6 | 17.3 |
| 25 | 7.1 | 10.7 | 18.4 |
| 27 | 7.1 | 11.0 | 20.4 |
| 29 | 7.1 | 11.4 | 22.4 |

In one embodiment, the crimp angle is between about 25-35°, and more particularly about 30°. It should be noted that as valve size increases, the height of the anchoring stent does not necessarily continue to increase. That is, there is a linear height increase between valve sizes 19-23 mm, but the height of the pre-crimped tube for valve sizes 25-27 mm is the same. Upon expansion, the portion of the stent frame 80 that is below the valleys 93a expands outward from the shape seen in FIG. 21A to the flared shape seen in FIG. 21B. The angle of the outward flare depends on the extent of balloon or mechanical finger expansion, but is preferably between about 10-20° from vertical, more preferably about 14°. This means that the diameter D of the lower end extends outward from the pre-crimped tubular diameter by between about 2-5%, more preferably about 3%. For instance, a 27 mm valve has an expanded lower end with a diameter D of about 28 mm. However, as mentioned elsewhere the surgeon may want to over-expand the surrounding annulus, and thus the expanded diameter D is variable depending on the procedure.

In a preferred assembly sequence, the stent frame 80 is crimped into the contracted configuration prior to covering with fabric to form the anchoring skirt 26, and prior to attaching to the valve member 24. That is, the purely conical shape shown in FIG. 19B or the tubular-conical configuration of FIG. 21A are formed by bending the stent frame 80 in a crimping device (not shown).

Figure 22B:
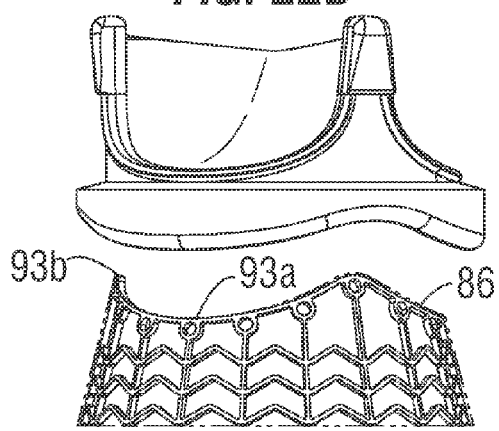

FIGS. 22A and 22B illustrate an exemplary prosthetic heart valve 20 both assembled and with a conical anchoring skirt 26 exploded from the valve component 24 and in its expanded state. Note again that the anchoring skirt 26 is wholly conical in both its contracted and expanded configurations, as with the stent 80 shown in FIG. 19B.

Figure 23A:
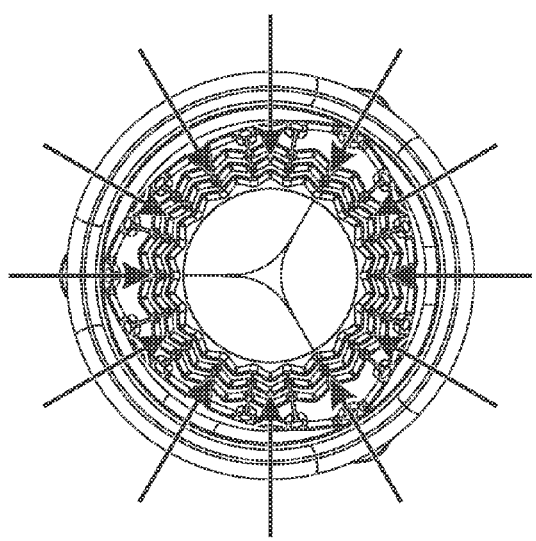
FIGS. 23A-23B and 24A-24B are views of the exemplary prosthetic heart valve schematically showing methods for crimping the expandable skirt into a conical delivery configuration after attachment to a valve member.
Figure 23B:
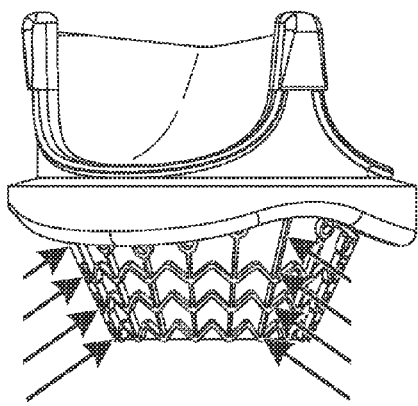
Figure 24A:
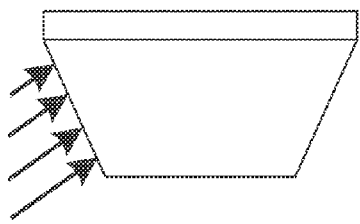

Although a preferred sequence is to crimp the stent frame 80 prior to covering with cloth, the cloth-covered stent frame 80 may be tubular when attached to the valve member 24, and then crimped into the conical shape shown in FIGS. 23A and 23B in a first crimping step (shown without the cloth cover). Preferably, a distributed inward crimping force is applied at even locations around the stent frame 80, such as indicated by the arrows in the figures. The frame 80 is fixed along and thus pivots inward about its scalloped upper end 86. The crimping forces are applied starting at about the level of the valleys of the uneven upper end 86, as schematically indicated in FIG. 24A, leaving a short axial distance where the stent frame 80 remains cylindrical, as shown in FIG. 21A.

Figure 24B:
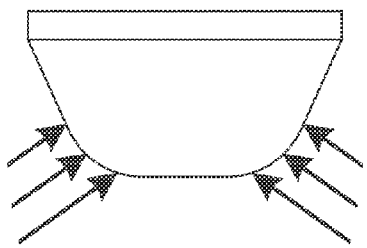

In an optional second crimping step, shown in FIG. 24B, inward forces are applied unevenly to curl the lower or distal end of the stent frame 80 inward, resulting in a somewhat spherical distal end. To avoid causing overlap between the struts of the plastically-expandable stent frame 80, the forces are desirably applied more at three locations distributed 120° apart so that a bottom plan view (see FIG. 7D) shows the lower end having a trilobular shape rather than circular. This helps reduce the leading end profile of the valve without compromising the ability of the stent frame 80 to freely expand into the shape in FIG. 22A. Regardless of the crimping method, the inflation balloon 112 ultimately outwardly expands the inflow end of the stent frame 80 to form the conical shape of FIGS. 22A and 22B, or the outwardly flared shape of FIG. 21B.

Figure 25:
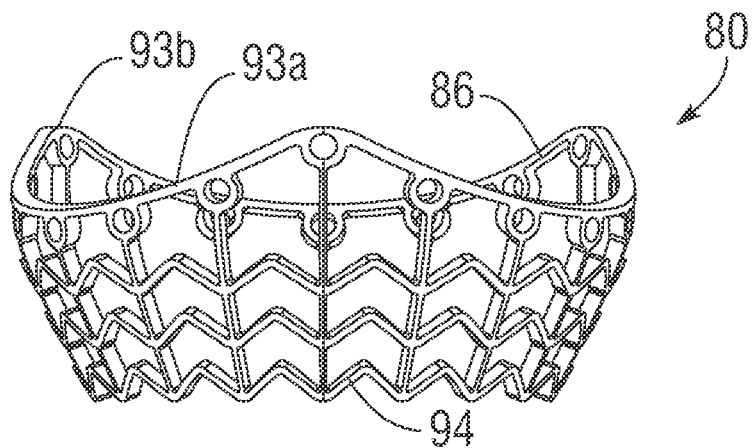
FIG. 25 is an elevational view of an exemplary anchoring skirt in a contracted state after a first crimping step.
Figure 25A:
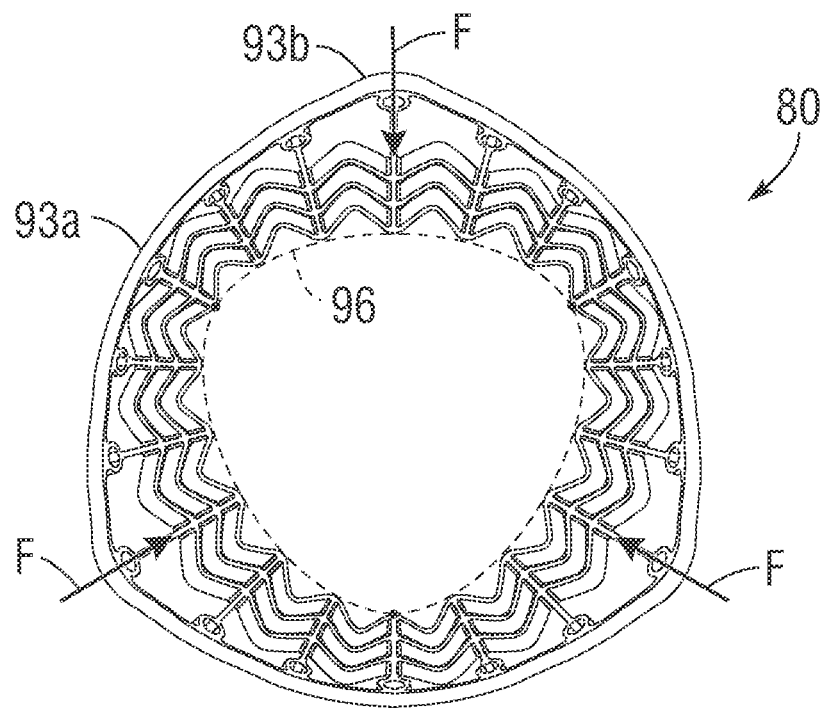
FIG. 25A shows the stent from a lower or inflow end after a second crimping step to create a tri-lobular inflow opening.

FIG. 25 is another elevational view of the exemplary stent frame 80 with a front peak 93b of the upper end 86 centered and in a contracted state after a first crimping step. The portion of the stent frame 80 above the valleys 93a are held firmly and the portion below is forced inward to a conical shape as shown, resulting in the tubular-conical shape as also seen in FIG. 21A. In a preferred second crimping step, inward forces F are applied at three locations as shown in FIG. 25A to create a tri-lobular inflow opening 96. Preferably the inward forces F are applied along the axially-extending struts 100 that are directly below and in-phase with the three peaks 93b. This means that the lower portion of the stent frame 80 will be crimped inward the most at the circumferential locations of the three peaks 93b, and the opening 96 thus has rounded apices aligned with the three valleys 93a. The purpose of the secondary crimping is to reduce the profile of the skirt 26 further to facilitate ease of positioning the framed valve inside the aortic valve annulus. That is, after the $1^{st}$ stage (conical)

crimping, the frame 80 outflow end adjacent the sewing ring 62 maintains its original cylindrical shape, which may hinder insertion of the valve down inside the aortic annulus. Additionally, the contour shape of the valleys 93a of the upper end 86 of the stent frame 80 must remain, since the frame's mating profile with the valve must be maintained. Therefore, to further reduce the frame 80 profile the diameter at the three peaks 93b is reduced by the $2^{nd}$ crimping step 1n doing so, the contour shape at the valleys 93a is preserved whereas the frame's overall profile is further reduced.

FIGS. 26-31 illustrated number of exemplary steps in covering the stent frame 80 with two different types of fabric to form an anchoring skirt 26.

Figure 26A:
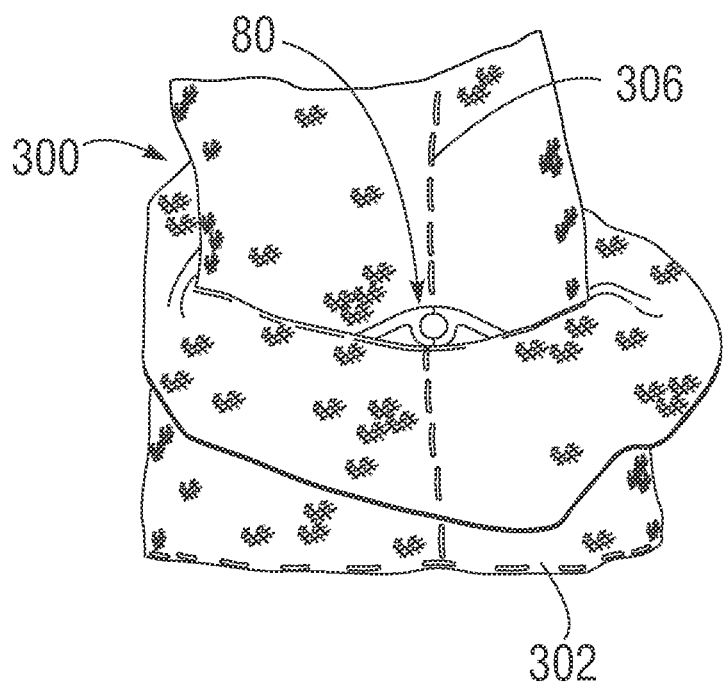
Figure 26B:
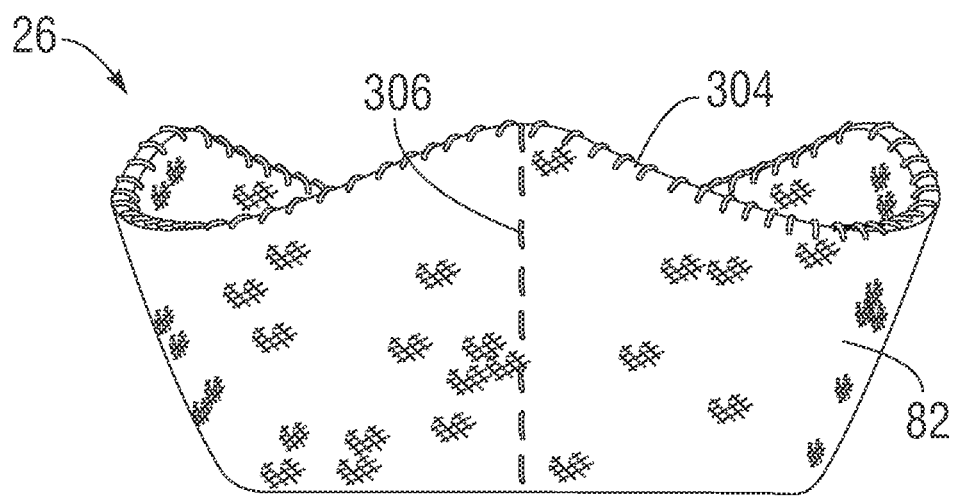
FIG. 26B shows the covered skirt.

FIG. 26A shows an assembly step where a tubular piece of fabric 300 is folded approximately at a midline 302 and the stent frame 80 placed in between the folded layers so that the lower end 94 rests in the fold crease where a stitch line is added. The piece of fabric 300 is then sewn along a stitch line 304 over the undulating top end 86 and trimmed, or vice-versa, so that FIG. 26B shows the covered skirt 26. It should be noted that the tubular piece of fabric 300 desirably has an axial seam 306 that is preferably aligned with the peaks 93b of the stent upper end 86, and thus with the commissures 35 of the heart valve member 24.

In a preferred embodiment, the fabric 82 immediately covering the stent 80 (inner fabric layer) comprises polytetrafluoroethylene (PTFE) cloth, such as Teflon, although other biocompatible fabrics may be used. More particularly, the fabric 82 is a PTFE flat yarn obtained from Atex Technologies Inc. of Pinebluff, N.C. Conversely, the sealing flange 84 comprises a much thicker material to provide prevention of paravalvular leakage. For instance, the sealing flange 84 is formed of a plush polymer, and made of polyethylene terephthalate (PET). More preferably, the material of the sealing flange 84 has a base yarn which is flat yarn 40/27, and a loop yarn extending therefrom made from PET 70/12 textured yarn both obtained from Atex Technologies Inc. of Pinebluff, N.C. The thickness of the sealing flange 84 material is desirably about 1.2 mm, uncompressed, while the thickness of the fabric 82 may be 50% or less of that. In alternative embodiments, different materials can be used from the covering layer 82 and the sealing layer 84, such as PTFE/cloth, cloth/cloth, or PTFE or cloth for the covering layer 82 and a swellable hydrophilic polymer such as an acrylic for the sealing layer 84.

FIGS. 27A-27B show opposite sides of a strip 310 of plush fabric used to create a sealing flange 84 on the expandable anchoring skirt 26. The material of the strip 310 includes a relatively smooth side 312 with rows of ribs of the fabric weave, and a plush or relatively fluffy side 314 with outwardly projecting loops and loose threads of the polymer material.

The strip 310 is then looped with the smooth side 312 outward and the free ends sewn together to form a ring 316, as shown in FIG. 28. FIGS. 29A-29C show several steps in folding and sewing the ring 316 of fabric into a double-layer sealing flange ring 318. More specifically, the single layer ring 316 is folded along an axial midline as in FIG. 29A so that the smooth side 312 is on the inside and the fluffy side 314 on the outside. The folded structure is then stitched together with sutures 318 to form the fluffy sealing flange ring 318.

Figure 30:
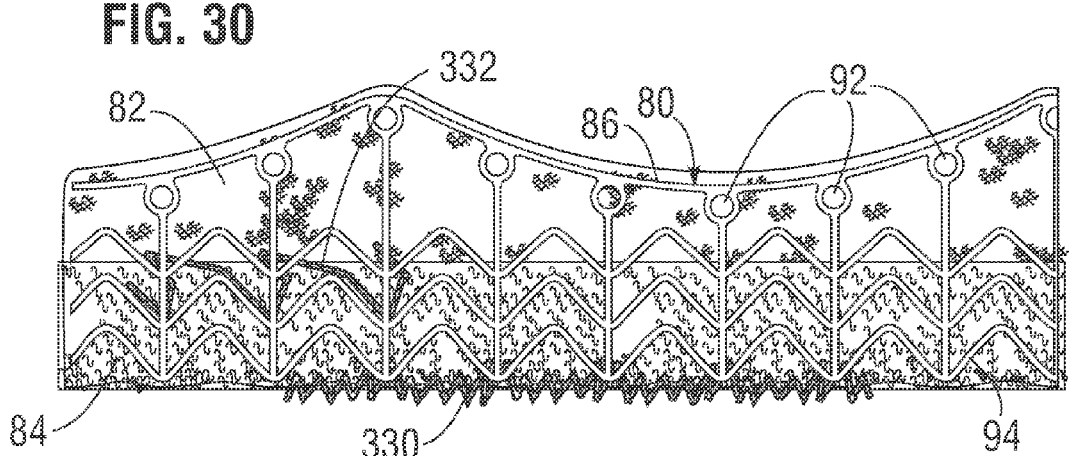
FIG. 30 shows a section of the anchoring skirt of FIG. 25 flattened and superimposed over a fabric covering and a sealing flange, and showing exemplary stitch locations for the sealing flange.

FIG. 30 shows a section of the stent frame 80 of FIG. 25 flattened and superimposed over a layer of the fabric covering 82 and the sealing flange 84. The lower edge 94 of the stent frame 80 is the inflow end and projects away from the valve member 24 (see FIG. 20), while the undulating upper edge 86 contacts and conforms to the valve member sewing ring 62. The inner fabric covering 82 is shown enclosing the stent frame 80, while the sealing flange 84 (in the form of the fluffy ring 318) is sewn to the covering 82 at stitch lines 330 and 332. The final anchoring skirt 26 is seen in FIG. 31C.

Figure 31A:
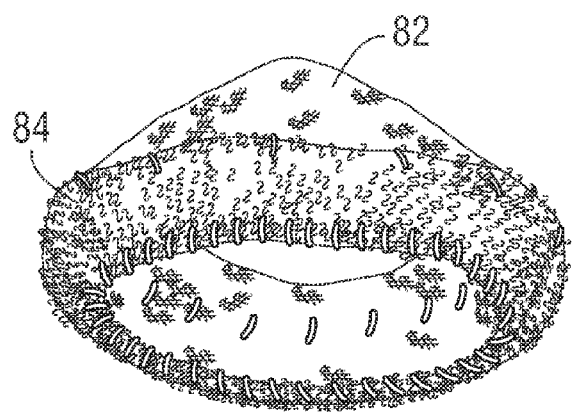
FIGS. 31A-31C are several views of the cloth covered anchoring stent with the sealing flange sewn thereon.
Figure 31B:
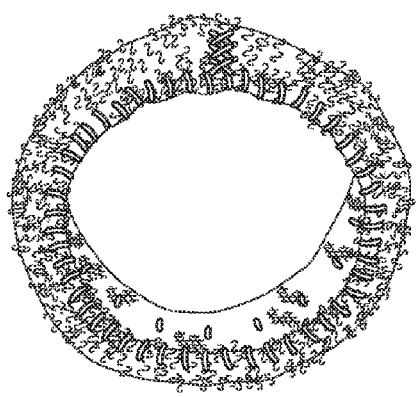
Figure 31C:
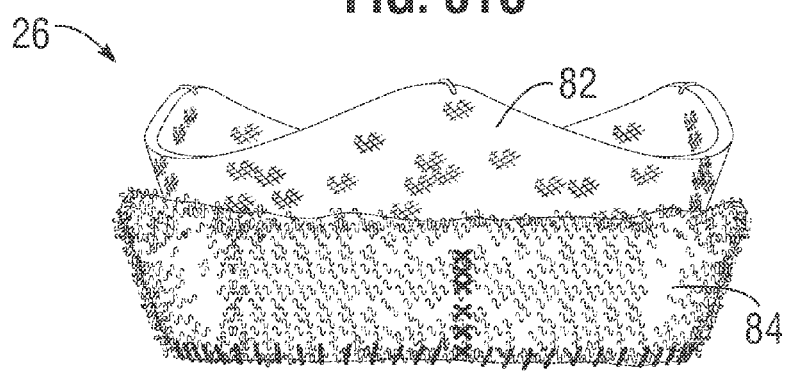

Now with reference to FIG. 32, an exemplary tissue valve member 24 is coupled to the with the anchoring skirt assembly 26 of FIG. 31C using connecting sutures 334. Again, the sutures 334 desirably attach to the valve member sewing ring 62 and loop through the eyelets 92 arrayed along the upper edge 86 of the inner stent frame 80 (see FIG. 30). FIG. 33 then shows attachment of an exemplary valve holder 22. With reference also to the details of FIGS. 6A and 6B, the connecting sutures 334 are passed through fabric at the cusps 34 of the prosthetic valve member 24, through holes 37 in the holder legs 32, and across a cutting guide in each leg. Note the position of the sealing flange 84 in a generally constant height ring 318 at the inflow or distal end of the anchoring skirt 26, which provides good contact with the surrounding ventricular walls and good paravalvular leak prevention.

FIG. 34 schematically illustrates the coupling of a tissue valve member 24 with an alternative anchoring skirt assembly 26' to form a heart valve 20'. In this embodiment, the entire exterior of the anchoring skirt assembly 26' is covered with the plush sealing flange material, including up to the tips of the stent peaks. FIG. 35 shows attachment of an alternative valve holder 22' to the combined heart valve 20', wherein the holder attaches to tips of the valve member commissures as opposed to along the valve cusps.

FIGS. 36A-36B are radial cross-sections parallel to the axis of a heart valve showing construction of an exemplary cloth covering of an anchoring skirt 26. In these figures, the anchoring skirt is schematically shown tubular (vertical in cross-section) for simplicity, though as mentioned above the inner stent frame 80 will preferably be crimped to a contracted at least partly conical shape prior to assembly with the valve member 24. Also, it should be noted that the cross-section is three cusp portion of the valve member 24, as opposed to through an upstanding commissure post.

With reference first to FIG. 36A, elements of the valve member 24 will be given the same numbers as described above, in particular with reference to FIGS. 15 and 15A. An outer edge of a flexible leaflet 74 is sandwiched between the cloth-covered wireform 50 and the band subassembly 40 with its outwardly-projecting sewing ring 62. The band subassembly 40 includes the two structural bands 42, 48 encompassed by a fabric cover 64. Various forms of sewing ring 62 are contemplated; the illustrated embodiment includes an inner suture permeable member 68 (e.g., silicone) having a frustoconical form and encompassed by a fabric cover 70. The same structure minus the wireform and leaflet will be repeated in all the FIGS. 36-41.

The anchoring skirt 26 comprises the structural stent 80 having the fabric cover 82 and the sealing flange 84. In the illustrated embodiment, the sealing flange 84 comprises a plush fabric that is folded in half at the bottom with the free edges at the top sewn together. This structure is the same as the ring 318 shown in FIG. 29C formed by the strip of material 310 folded and sewn upon itself as described above. That is, the sealing flange 84 comprises a double layer of textured cloth. Although not shown, the sealing flange 84 will be stitched to the fabric cover 82 at both its top and bottom ends. As mentioned, the sealing flange 84 surrounds the lower end of the stent frame 80 but does not extend all way up to the top end. In one embodiment, the height of the sealing flange 84 is approximately 7 mm.

In FIG. 36B, the anchoring skirt 26 comprises the fabric cover 82 completely surrounding the stent frame 80, while the sealing flange 84 includes a folded double layer 320 of textured fabric at the inflow or lower end, and a single layer 322 of textured fabric extending upward into the vicinity of the sewing ring 62. Both the folded double layer 320 and single layer 322 are desirably formed of the same panel of material. This arrangement covers the entire exterior of the anchoring skirt 26, while providing a thicker sealing flange 84 around the inflow end thereof than around the upper end in contact with the valve member. As mentioned, reducing the thickness of the anchoring skirt 26 in the vicinity of the valve member 24 helps conform to the surrounding shelf-like annulus. It should also be noted that the fabric cover 82 has a circumferential seam at about its midpoint along the stent frame 80, and the double layer 320 is below that seam to avoid creating a bulge.

FIG. 37A illustrates an alternative sealing flange 84 that becomes gradually thicker away from the valve member 24. That is, the sealing flange 84 is formed from a single panel of textured material attached on the exterior of the fabric cover 82 that has a radially thin region 324a adjacent the valve member, an intermediate thickness region 324b below that, and a thickened region 324c adjacent the lower or inflow end. Again, this provides good sealing against paravalvular leakage and accommodates the inwardly protruding annulus just below the valve member. The regions 324a, 324b, and 324c are separated by steps in the material, rather than being gradual transitions. In one embodiment, the thickness of the regions 324a, 324b, and 324c increases by doubling after each step from the upper end to the lower end. The fabric cover 82 surrounds the stent frame 80, which is the same as the embodiment shown in FIG. 37B, however the alternative sealing flange 84 comprises a wedge-shaped panel of material 326 having a gradually increasing thickness from the upper to lower end.

FIG. 37C illustrates a still further anchoring skirt 26 having a modified fabric cover 82' that extends only on the interior of the stent frame 80. A sealing flange 84 includes a stepped panel 328 of textured material much like the stepped panel of FIG. 37A. Either the ends of the fabric cover 82' or the ends of the panel 328 extend around the stent frame 82 and are secured with seams. FIG. 37D illustrates a similar anchoring skirt 26 having a sealing flange 84 comprising a stepped panel 330 of textured material, but no fabric cover around the stent frame 80. Instead, the panel 330 extends around the inside of the stent frame as well as on the outside.

Figure 38A:
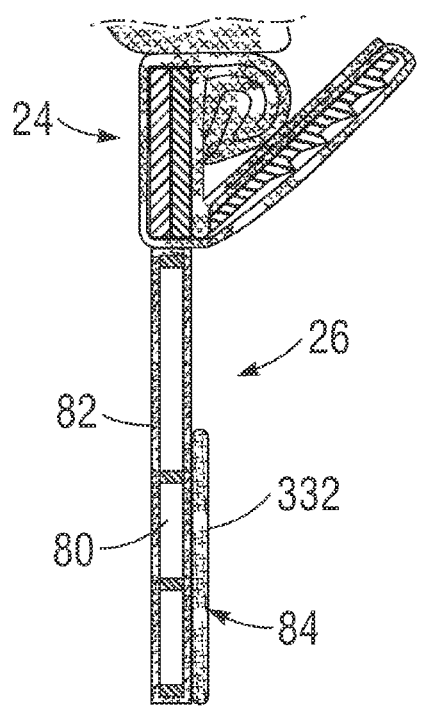
FIGS. 38A-38B are radial cross-sections similar to FIGS. 36A-36B showing a single-layer sealing flange in different axial locations.
Figure 38B:
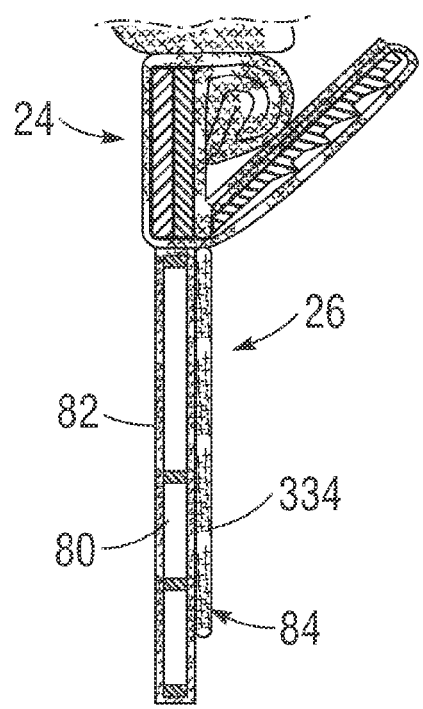
Figure 39A:
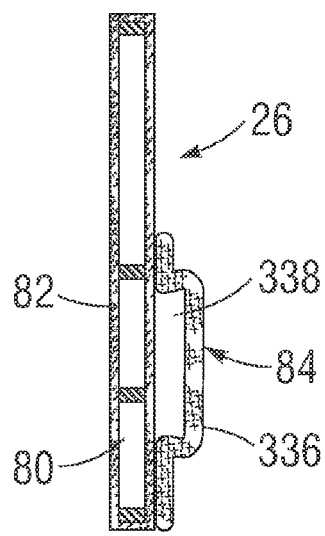
Figure 39B:
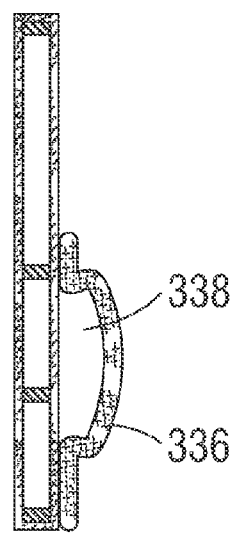
Figure 39C:
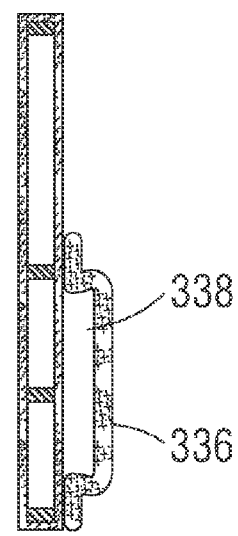

FIGS. 38A and 38B both illustrate a single-layer sealing flange 84 in different axial locations. Namely, FIG. 38A shows a single layer panel 332 of textured material forming the sealing flange 84 on the exterior of a fabric cover 82 that surrounds the stent frame 80. The panel 332 extends from the lower end of the anchoring skirt 26 upward to around the midsection of the skirt, leaving a region adjacent the valve member 24 with only the fabric cover 82. In contrast, FIG. 38B shows a single layer panel 334 of textured material attached on the exterior of the fabric cover 82 and extending downward from the upper end of the anchoring skirt 26, but stopping short of the lower end. A single layer panel of textured material reduces the overall thickness of the anchoring skirt 26 for better conformity within the annulus, while still providing good prevention of paravalvular leakage.

FIGS. 39A-39J are radial cross-sections of alternative anchoring skirts with a variety of different folded sealing flanges 84 that are located adjacent the lower end of the anchoring skirt 26. Without going into explicit detail about each one, the sealing flanges 84 are each formed of single panels 326 of textured material that are attached to the exterior of a fabric cover 82 surrounding the stent frame 80. Some of the panels are attached at both ends with a portion between vaulted away from the fabric cover 82, such as in FIGS. 39A-39C. The cavities created by vaulted panels may be filled with material, such as absorbent fabric, swellable polymer, fibrin glue, or other such components that enhance the capacity for sealing against paravalvular leakage. The ends of the panels may be attached flat against the fabric cover 82, or maybe folded in so as to form portions where there are double layers of material, such as in FIGS. 39D-39J. Alternatively, one end may be attached flat against the fabric cover 82, while the other end is folded in, such as in FIGS. 39D, 39H, and 39J.

Figure 40A:
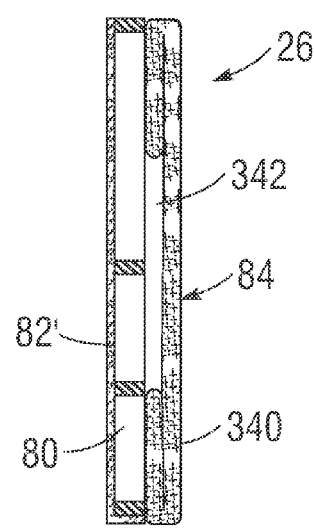
FIGS. 40A-40C are radial cross-sections of a schematic tubular anchoring skirt with a cloth-covering having a single layer inside the anchoring skirt and an outer sealing flange.
Figure 40B:
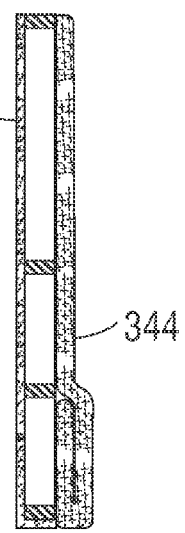
Figure 40C:
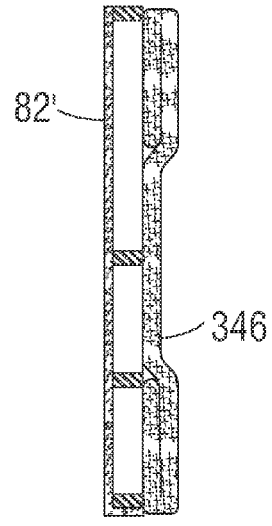

FIGS. 40A-40C illustrate alternative anchoring skirts 26 each of which has a fabric cover 82' on only the interior of the stent frame 80, and an exterior sealing flange 84 that extends the entire height of the skirt. In FIG. 40A, a single panel 340 of textured material is folded at both ends at the upper and lower ends of the stent frame 80. The cavity 342 is left between the panel 340 and the stent frame 84 for filling with some sort of sealing material. In FIG. 40B, single panel 344 of textured material extends the length of the stent frame 80, and is folded in only at the lower end. Finally, in FIG. 40C, a single panel 346 of textured material covers the entirety of the stent frame 80 and is folded in at both ends. The panel 346 attaches to the stent frame 80 without cavities therebetween.

Figure 41A:
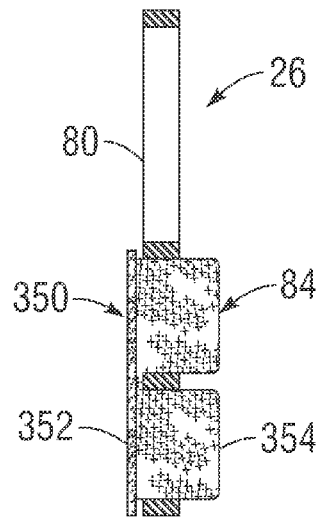
FIGS. 41A-41C are radial cross-sections of a schematic tubular anchoring skirt with a single layer of plush fabric attached inside the anchoring skirt and extending through the stent frame apertures to form a sealing flange on the outside thereof.
Figure 41B:
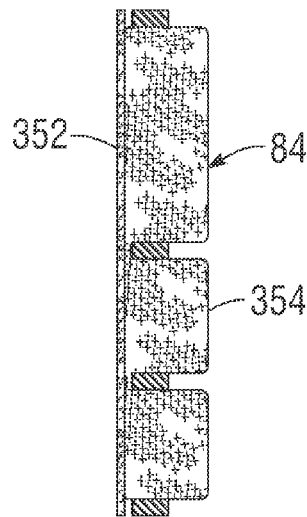
Figure 41C:
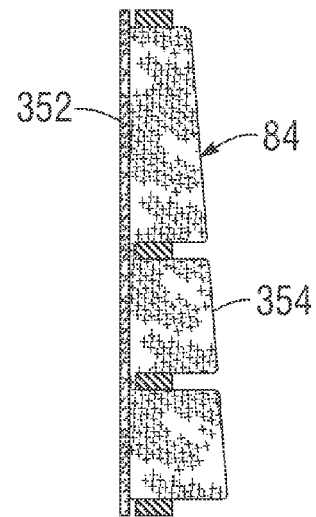

FIGS. 41A-41C illustrates still further anchoring skirts formed without a fabric cover 82 as described above, and with only a single layer of plush fabric attached on the inside of the stent frame 80. For example, FIG. 41A shows a single layer of textured fabric 350 attached on the inside of the stent frame 80 at the lower end thereof. The textured fabric 350 includes a base panel 352 and a fluffy portion 354 formed by a plurality of looped fibers. The fluffy portion 354 projects through apertures in the stent frame 82 the exterior thereof, thus forming a sealing flange 84. In FIG. 41B, the textured fabric 350 extends the length of the stent frame 80, and projects through the apertures evenly from top to bottom. In FIG. 41C, the textured fabric 350 also extends the length of the stent frame 80, but the fluffy portion 354 has a gradually increasing thickness from the top to the bottom end so as to form a tapered sealing flange 84. By providing the textured fabric 350 only on the inside of the stent frame 80 and projecting therethrough, the overall radial dimension of the anchoring skirt 26 may be reduced while still providing good paravalvular leak protection.

Figure 42:
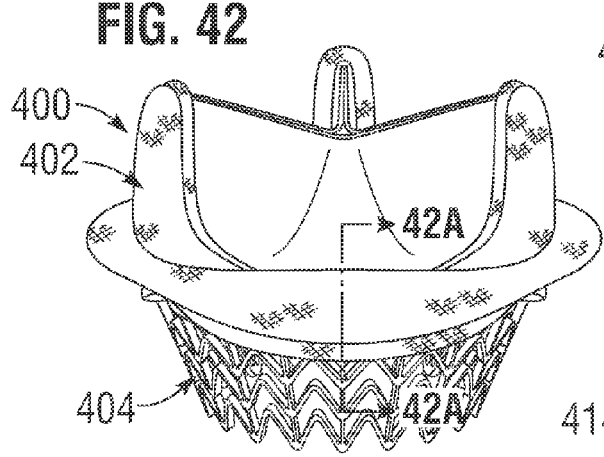
FIG. 42 is a perspective view of an exemplary prosthetic heart valve having commercially available valve components coupled with a skirt stent minus a surrounding fabric cover.
Figure 42A:
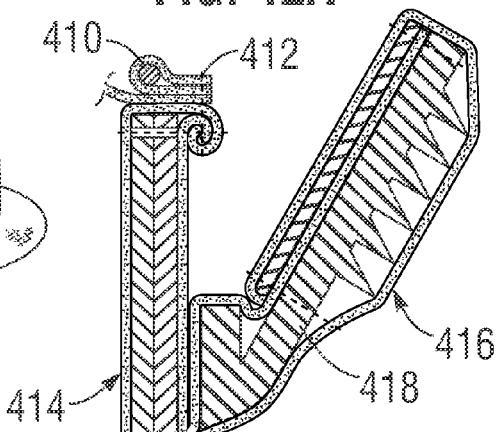
FIG. 42A is a radial sectional view through a cusp portion of the heart valve with the fabric cover of the skirt stent shown.
Figure 43:
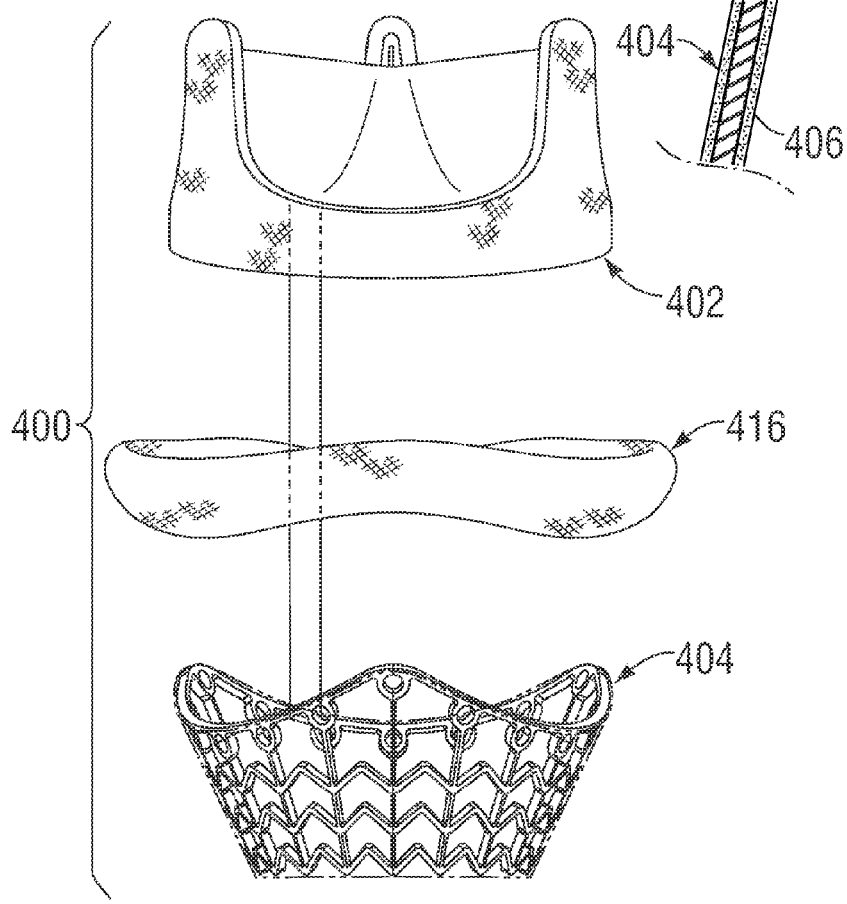
FIG. 43 is an exploded elevational view of the prosthetic heart valve of FIG. 42.

Various heart valves may be utilized in combination with the delivery system components described herein, and any combination not otherwise explicitly described is contemplated. For instance, FIG. 42 is a perspective view of an exemplary prosthetic heart valve 400 having a commercially available valve member 402 coupled with an anchoring stent 404 minus a surrounding fabric cover. FIG. 42A is a radial sectional view through a cusp portion of the heart valve 400 with a fabric cover 406 of the skirt stent 404 shown. Finally, FIG. 43 is an exploded elevational view of the prosthetic heart valve 400 of FIG. 42. The particular valve member 402 shown is the Carpentier-Edwards PERIMOUNT Magna® Aortic Heart Valve available from Edwards Lifesciences of Irvine, Calif.

As seen in FIG. 42A, the Magna valve has a structure including a wireform 410 wrapped in a cloth cover 412 and attached to a cloth-covered axial band structure 414 with flexible bioprosthetic leaflets 414 sandwiched therebetween. A highly flexible sewing ring 416 attaches to the outside perimeter of the band structure 414 as shown. Finally, the cloth-covered anchoring skirt 404 is secured at a butt joint to an inflow end of the Magna valve, such as with sutures through the respective cloth covers and desirably through the stent frame of the skirt 404 and through apertures in the band structure 414, as described above. The sewing ring 416 attaches to the band structure 414 along a line of stitching, rendering it easily flexed outward. Further, the sewing ring 416 has a relatively thin-walled silicone insert 418 with a honeycomb structure. That is an advantage for conventional valves, but may not be quite so desirable for valves as described herein.

Figure 44:
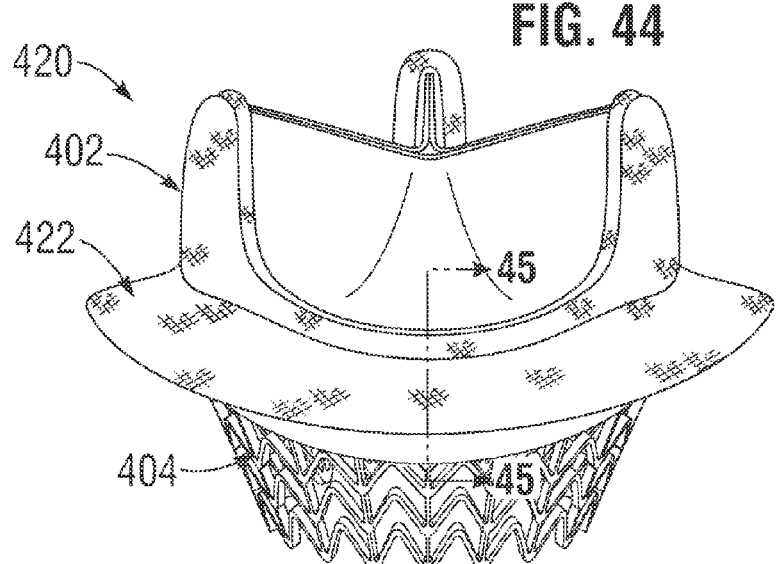
FIG. 44 is a perspective view of an alternative prosthetic heart valve similar to that shown in FIG. 42 but having a different firmer sewing ring.
Figure 45A:
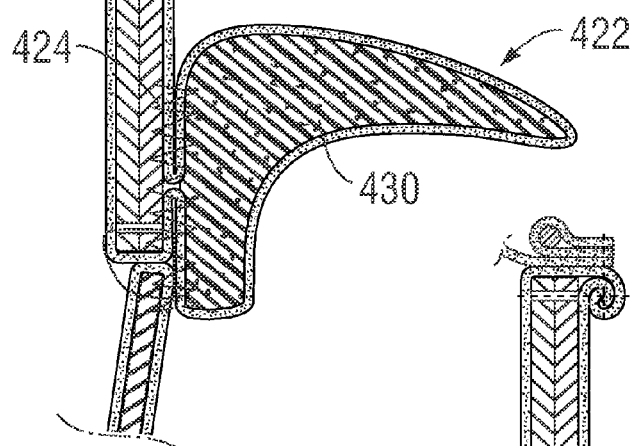
FIGS. 45A and 45B are radial sectional views through the prosthetic heart valve of FIG. 44 illustrating alternative constructions.
Figure 45B:
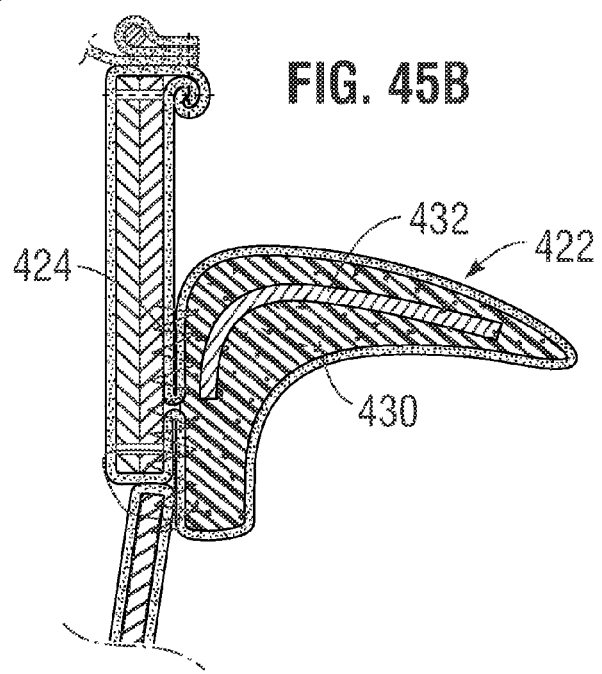

In contrast, FIG. 44 shows an alternative prosthetic heart valve 420 similar to that shown in FIG. 42 but having a different, firmer sewing ring 422. In particular, FIGS. 45A and 45B are radial sectional views through the prosthetic heart valve 420 illustrating alternative constructions of the sewing ring 422. Like elements will be given like numbers.

In both FIGS. 45A and 45B the sewing ring 422 secures to the outside of the band structure 414 along a cylindrical region of stitching 424, which helps reduce up and down flexing of the sewing ring 422. Secondly, the sewing ring 422 in FIG. 45A comprises a solid yet compressible material that is relatively stiff so as to provide a seal against the annulus and has a concave inflow shape that conforms to the annulus. Desirably, the sewing ring 422 includes a closed-cell foam insert 430 within a cloth cover. There are no cavities/cells, which makes the sewing ring 422 soft to the surrounding tissue yet relatively stiff overall. Moreover, the concave inflow side matches that of the annulus for better sealing therebetween. FIG. 45B shows an additional reinforcing member 432 embedded within the insert 430 that stiffens the sewing ring 422 even further. The reinforcing member 432 may be metallic, such as stainless steel or the like. Both sewing rings 422 are stiffer than the Magna sewing ring and thus create a better seal against the aortic valve annulus in opposition to the outwardly expanded anchoring skirt within the left ventricle. The combination provides a relatively secure anchoring structure for the valves disclosed herein, and helps prevent paravalvular leaking around the outside of the valve by matching the shape of and firmly holding the soft material against the annulus.

Once again, the cloth-covered anchoring skirt 404 is secured at a butt joint to an inflow end of the Magna valve, such as with sutures through the stent frame of the skirt 404 and through apertures in the band structure 414. Furthermore, the lower end of the sewing ring 422 desirably overlaps the anchoring skirt 404 by a short distance and the stitching 424 extends down therebetween. This further enhances the stiffness of the assembly, thus improving seating and sealing against the aortic annulus. Although not shown, the sewing ring 422 may be annular but is desirably slightly scalloped so as to better conform to the aortic annulus. The stiff scalloped sewing ring 422 assists the surgeon in rapidly seating the prosthetic valve in place by providing a firm platform to mate against the contours of the undulating aortic annulus.

It should be noted that a sewing ring per se may not be necessary with the present heart valve as the primary function of such a component is to provide a platform through which to pass a number of anchoring sutures around the valve periphery, which is not used here except perhaps for several (e.g., 3) guide sutures. Consequently, the valve members described herein could be coupled to the anchoring skirt directly without a sewing ring. To help prevent paravalvular leaking a peripheral seal such as a fabric skirt as described above may be added in place of the sewing ring. Also, several tabs extending outward from the valve structure could be used for anchoring the guide sutures which take the place of the sewing ring for that purpose.

The system disclosed herein is also desirably used with a particular valve annulus sizing technique. The sizing apparatus (not shown) includes a catheter shaft having a compliant balloon on a distal end that can be inflated with saline. An intravascular ultrasound (IVUS) imaging probe extends through the catheter and within the compliant balloon. After preparing the patient for surgery, but prior to introduction of the delivery system 110, the balloon catheter is introduced into the valve annulus. The balloon is filled to a desired pressure, and the IVUS probe is advanced through the catheter and into the balloon. Because the balloon conforms to the anatomical cavity surrounding it, the IVUS probe measures the size of that cavity.

The advantage of being able to expand the native annulus with the expandable skirt to receive a larger valve size than would otherwise be possible with conventional surgery was mentioned above. Another way to accomplish such enlargement is to utilize a tapered dilator, such as a Hagar dilator. The conical dilator has a maximum diameter that is larger than the anticipated valve diameter. By passing the dilator into the annulus prior to installation of the valve, a larger valve may be selected. Furthermore, the larger valve temporarily fits within the annulus, but the resiliency of the tissue constricts around the valve for a more secure anchor.

While the invention has been described in its preferred embodiments, it is to be understood that the words which have been used are words of description and not of limitation. Therefore, changes may be made within the appended claims without departing from the true scope of the invention.

What is claimed is:

1. A prosthetic heart valve for implant at a heart valve annulus, comprising:
   a non-expandable, non-collapsible annular support structure defining a flow orifice and having an inflow end;
   valve leaflets attached to the support structure and mounted to alternately open and close across the flow orifice;
   a plastically-expandable stent frame terminating in a first end extending around the flow orifice and connected to the valve at the inflow end of the support structure, the stent frame terminating in a second end projecting in the inflow direction away from the support structure and being capable of assuming a contracted state for delivery to an implant position and a wider expanded state for outward contact with an annulus; and
   a fabric covering around the stent frame including an enlarged sealing flange connected to an exterior surface of the fabric covering and surrounding at least the second end to contact the annulus and prevent paravalvular leaking, wherein the fabric sealing flange comprises a strip of textured PET fabric that has a smooth side and a plush textured side, and the strip is connected at free ends to form a ring and folded in half about its midsection and having its free circumferential ends connected at a seam so that the smooth sides face toward each other and plush textured sides face away from each other.

2. The heart valve of claim 1, wherein in the contracted state the stent frame is conical, tapering inward from the first end toward the second end.

3. The heart valve of claim 2, wherein in the expanded state the stent frame is conical, tapering outward from the first end toward the second end.

4. The heart valve of claim 1, further including a sewing ring circumscribing the inflow end of the support structure, wherein the stent frame attaches to the sewing ring.

5. The heart valve of claim 4, wherein the sewing ring comprises a solid yet compressible material that is stiff so as to provide a seal against the annulus and has a concave inflow shape that conforms to the annulus.

6. The heart valve of claim 1, wherein the sealing flange extends in a ring only around the second end of the stent frame and does not extend up to the first end.

7. The heart valve of claim 1, wherein the sealing flange covers the entire exterior of the stent frame.

8. The heart valve of claim 1, further including a sewing ring circumscribing the inflow end of the support structure and having an undulating shape that matches the shape of the first end of the stent frame, and the first end of the stent frame attaches to the sewing ring with sutures.

9. The heart valve of claim 8, wherein the stent frame first end has peaks and valleys that match the sewing ring, and the stent frame in the contracted state extends away from the sewing ring in a tubular portion between the peaks and valleys and then angles inward in a conical portion to the second end.

10. A prosthetic heart valve for implant at a heart valve annulus, comprising:
    a non-expandable, non-collapsible annular support structure defining a flow orifice and having an inflow end;
    valve leaflets attached to the support structure and mounted to alternately open and close across the flow orifice;
    a plastically-expandable stent frame having a first end extending around the flow orifice and connected to the valve at the inflow end of the support structure, the stent frame having a second end projecting in the inflow direction away from the support structure and being capable of assuming a contracted state for delivery to an implant position and a wider expanded state for outward contact with an annulus, wherein the stent frame has an undulating first end with peaks and valleys that conform to a shape of the inflow end of the support structure, and the stent frame in the contracted state extends away from the inflow end of the support structure in a tubular portion between the peaks and valleys and then angles inward in a conical portion to the second end, wherein in the contracted state the stent frame angles inward in a conical portion and the second end defines an orifice that is non-circular, and wherein the second end is circular when in the expanded state; and
    a fabric sealing flange attached to the stent frame comprising a strip of textured PET fabric that has a smooth side and a plush textured side, and the strip is connected at free ends to form a ring and folded in half about its mid-section and having its free circumferential ends connected at a seam so that the smooth sides face toward each other and plush textured sides face away from each other.

11. The heart valve of claim 10, wherein in the contracted state the stent frame second end defines an orifice that is a shape with three lobes.

12. The heart valve of claim 10, further including a sewing ring circumscribing the inflow end of the support structure and having an undulating shape that matches the shape of the first end of the stent frame and attaches thereto with sutures.

13. The heart valve of claim 10, wherein the fabric sealing flange extends in a ring only around the second end of the stent frame and does not extend up to the tubular portion.

14. The heart valve of claim 10, wherein the fabric sealing flange covers the entire exterior of the stent frame.

15. The heart valve of claim 10, wherein the fabric sealing flange comprises a fabric panel located only on the interior of the stent frame and the plush textured side provides loops of material that project through apertures in the stent frame.

16. The heart valve of claim 10, wherein the fabric sealing flange has a gradually variable thickness which is thickest at the second end of the stent frame.

17. The heart valve of claim 10, further including a fabric cover surrounding the stent frame and to the exterior of which the sealing flange attaches.

18. A prosthetic heart valve for implant at a heart valve annulus, comprising:
    a non-expandable, non-collapsible annular support structure defining a flow orifice and having an inflow end;
    valve leaflets attached to the support structure and mounted to alternately open and close across the flow orifice;
    a plastically-expandable stent frame having a first end extending around the flow orifice and connected to the valve at the inflow end of the support structure, the stent frame having a second end projecting in the inflow direction away from the support structure and being capable of assuming a contracted state for delivery to an implant position and a wider expanded state for outward contact with an annulus; and
    a fabric covering around the stent frame including an enlarged sealing flange surrounding the second end to contact the annulus and prevent paravalvular leaking, wherein the sealing flange extends in a ring only around the second end of the stent frame and does not extend up to the first end, wherein the fabric sealing flange comprises a strip of textured PET fabric that has a smooth side and a plush textured side, and the strip is connected at free ends to form a ring and folded in half about its mid-section and having its free circumferential ends connected at a seam so that the smooth sides face toward each other and plush textured sides face away from each other.

19. The heart valve of claim 18, wherein in the contracted state the stent frame is conical, tapering inward from the first end toward the second end, and wherein in the expanded state the stent frame is conical, tapering outward from the first end toward the second end.

20. The heart valve of claim 18, wherein in the contracted state the stent frame angles inward in a conical portion and the second end defines an orifice that is non-circular, and wherein the second end is circular when in the expanded state.

21. The heart valve of claim 18, wherein the stent frame has an undulating first end with peaks and valleys, and further including a sewing ring circumscribing the inflow end of the support structure and having an undulating shape that matches the shape of the first end of the stent frame.

22. The heart valve of claim 18, wherein the stent frame in the contracted state extends away from the sewing ring in a tubular portion between the peaks and valleys and then angles inward in a conical portion to the second end.

* * * * *